United States Patent
Lin et al.

(10) Patent No.: US 10,647,682 B2
(45) Date of Patent: May 12, 2020

(54) SALTS OF 2,6-DIMETHYLPYRIMIDONE DERIVATIVES AND USES THEREOF

(71) Applicant: SUNSHINE LAKE PHARMA CO., LTD., Dongguan, Guangdong (CN)

(72) Inventors: Runfeng Lin, Dongguan (CN); Liang Chen, Dongguan (CN); Xiaojun Wang, Dongguan (CN); Yingjun Zhang, Dongguan (CN); Jiancun Zhang, Dongguan (CN)

(73) Assignee: NORTH & SOUTH BROTHER PHARMACY INVESTMENT COMPANY LIMITED, Wanchai (HK)

( * ) Notice: Subject to any disclaimer, the term of this patent is extended or adjusted under 35 U.S.C. 154(b) by 0 days.

(21) Appl. No.: 16/316,055

(22) PCT Filed: Jul. 19, 2017

(86) PCT No.: PCT/CN2017/093521
§ 371 (c)(1),
(2) Date: Jan. 8, 2019

(87) PCT Pub. No.: WO2018/019166
PCT Pub. Date: Feb. 1, 2018

(65) Prior Publication Data
US 2019/0308939 A1  Oct. 10, 2019

(30) Foreign Application Priority Data
Jul. 27, 2016 (CN) .......................... 2016 1 0598745

(51) Int. Cl.
C07D 239/22 (2006.01)
C07C 57/145 (2006.01)
C07C 317/22 (2006.01)
A61P 13/08 (2006.01)
A61P 1/16 (2006.01)
A61P 13/12 (2006.01)
A61P 17/00 (2006.01)
A61K 31/513 (2006.01)
A61P 25/28 (2006.01)
A61P 1/18 (2006.01)
A61P 11/00 (2006.01)
A61P 43/00 (2006.01)
C07D 239/36 (2006.01)

(52) U.S. Cl.
CPC .......... C07D 239/22 (2013.01); A61K 31/513 (2013.01); A61P 1/16 (2018.01); A61P 1/18 (2018.01); A61P 11/00 (2018.01); A61P 13/08 (2018.01); A61P 13/12 (2018.01); A61P 17/00 (2018.01); A61P 25/28 (2018.01); A61P 43/00 (2018.01); C07C 57/145 (2013.01); C07C 317/22 (2013.01); C07D 239/36 (2013.01); C07B 2200/13 (2013.01)

(58) Field of Classification Search
CPC .................................................... C07D 239/22
See application file for complete search history.

(56) References Cited

U.S. PATENT DOCUMENTS 8,232,408 B2  7/2012  Chen et al.
9,290,450 B2  3/2016  Kossen et al.
9,434,695 B2  9/2016  Zhang et al.

FOREIGN PATENT DOCUMENTS

CA           2872110 A1 * 1/2014
WO   WO-2014012360 A1 * 1/2014

OTHER PUBLICATIONS

Lederer. American Journal of Respiratory and Critical Care Medicine, 2012, 185, 697-98 (Year: 2012).*
ISR of PCT/CN2017/093521.
Written Opinion of PCT/CN2017/093521.

* cited by examiner

Primary Examiner — Noble E Jarrell
(74) Attorney, Agent, or Firm — Kam Wah Law

(57) ABSTRACT

Provided are salts of 2,6-dimethylpyrimidone derivatives and uses thereof. Also provided are pharmaceutical compositions containing the salts.

14 Claims, 12 Drawing Sheets

SALTS OF 2,6-DIMETHYLPYRIMIDONE DERIVATIVES AND USES THEREOF

CROSS REFERENCE TO RELATED APPLICATIONS

This is a U.S. national stage application of the International Patent Application No. PCT/CN2017/093521, filed Jul. 19, 2017, which claims priority to Chinese Patent Application No. 201610598745.1, filed Jul. 27, 2016, both of which are incorporated herein by reference in their entirety.

FIELD OF THE INVENTION

The present invention belongs to the drug field, relates to salts of 2,6-dimethylpyrimidone derivatives and uses thereof, specifically relates to salts of 3-(4-(dihexylamino)-3-fluorophenyl)-2,6-dimethylpyrimidin-4(3H)-one (compound I) and uses thereof, and further relates to pharmaceutical compositions containing the salts. The salts or the pharmaceutical compositions are used for treating and preventing a tissue or organ fibrosis disorder. The salts of the compound of the invention can be a crystal form, a part crystal form, a polymorphism or an amorphism.

BACKGROUND OF THE INVENTION

Fibrosis is a process of forming fibrous connective tissue overly in an organ or tissue for reparation or reaction. Slight fibrosis of organ or tissue is called fibrosis, severe fibrosis can cause damage of tissues leading to organ scarring. Tissue fibrosis is not only in lung, liver, heart, kidney, and the like tissue, but in all the organs and systems of the human body, about 1/3 persons in the world are dead from tissue fibrosis and organ failure caused by it.

Nitrogen heterocyclic derivatives having anti-fibrotic effects were disclosed in patent application WO2014012360 and CN103570630, wherein the compound 3-(4-(dihexylamino)-3-fluorophenyl)-2,6-dimethylpyrimidin-4(3H)-one (compound I) can prevent or treat tissues fibrosis lesion in a human or animal.

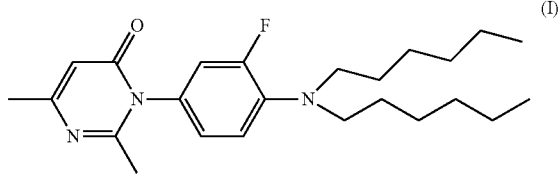 [SMILES: CCCCCCN(CCCCCC)c1ccc(-n2c(C)nc(C)cc2=O)cc1F]

Drug polymorphism is a common phenomenon in drug research, it is an important factor affecting drug quality. Various crystalline forms of the same drug have significantly different appearance, solubility, melting point, dissolution, bioavailability, and so on, also have different effects on stability, bioavailability and efficacy and so on. Therefore, the polymorphism problem of a drug should be considered overall in drug research.

Amorphism is a form in substance polymorphism phenomenon, it is an amorphous state. Various physicochemical properties and clinical efficacy characteristics of an amorphous drug are often different from those of a general crystalline drug. Therefore, a deep discuss for an amorphous substance is also important in polymorphism research of solid drugs.

SUMMARY OF THE INVENTION

Amino compound 3-(4-(dihexylamino)-3-fluorophenyl)-2,6-dimethylpyrimidin-4(3H)-one (the compound represented by formula I) is a pale yellow oil. In order to improve the stability and bioavailability of the compound, the present invention have studied on salts of compound (I) and crystalline forms thereof, and then provides a pharmaceutically acceptable acid addition salt of compound (I) and compositions thereof. The salts and the pharmaceutical composition have a better biological activity, a lower toxicity and a much better stability, and thereby have a better druggability. For example, the salts and the pharmaceutical composition have good pharmacokinetic properties, and/or less side effects of vomiting in dogs.

In particular, the present invention relates to acid addition salts of compound (I) and pharmaceutical compositions thereof, and uses of the salts of the compound and the pharmaceutical compositions in the manufacture of a medicament for preventing or treating a tissue fibrosis disorder. The acid addition salt disclosed herein can be a crystalline form, a part crystalline form, a polymorphism or an amorphism; in other aspect, the acid addition salt disclosed herein can be a solvate, such as a hydrate.

In one aspect, the present invention provides an acid addition salt of compound (I),

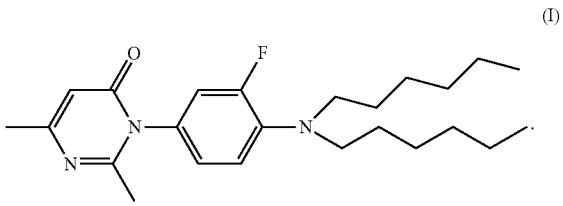 [SMILES: CCCCCCN(CCCCCC)c1ccc(-n2c(C)nc(C)cc2=O)cc1F]

In some embodiments, the acid addition salt provided herein is an inorganic acid salt or organic acid salt.

In some other embodiments, the inorganic acid salt provided herein is hydrochloride, sulfate, hydrosulfate, nitrate, hydrobromide, hydriodate, carbonate, bicarbonate, sulfite, bisulfite, pyrosulfate, hydrophosphate, dihydric phosphate, perchlorate, persulfate, hemisulphate, bisulphate, thiocyanate, phosphate, pyrophosphate, metaphosphate or a combination thereof.

In some other embodiments, the organic acid salt provided herein is formate, acetate, propionate, butyrate, benzoate, malonate, succinate, pyruvate, mesylate, ethanesulfonate, propanesulfonate, citrate, 4-nitrobenzoate, benzene sulfonate, tosilate, malate, propiolate, 2-butynoate, 2-hydroxy-ethanesulfonate, vinyl acetate, tartrate, L-tartrate, fumarate, hydroxy ethylene sulfonate, maleate, lactate, lactobionate, pamoate, salicylate, galactarate, gluceptate, mandelate, 1,2-ethanedisulfonate, naphthalenesulfonate, oxalate, trifluoroacetate, trifluoromethanesulfonate, adipate, suberate, sebacate, butyne-1,4-dioate, hexene-1,6-dioate, hydroxyacetate, alginate, ascorbate, erythorbate, aspartate, L-aspartate, glutamate, L-glutamate, 2-phenoxybenzoate, 2-(4-hydroxybenzoyl)benzoate, acetoacetate, 2-hydroxyethanesulfonate, borate, chlorobenzoate, camphorate, itaconate, camphorsulfonate, levocamphorsulfonate, methylbenzoate, dinitrobenzoate, sulfamate, galacturonate, cyclopentylpropanoate, dodecyl sulfate, acrylate, cypionate, glycerophosphate, methoxybenzoate, digluconate, gluconate, heptylate, hexanoate, 2-hydroxyethanesulfonate, pivalate, glucuronate, laurate, phthalate, phenylacetate, laurylsulfate, 2-acetoxybenzoate, nicotinate, cinnamate, oleate, palmitate, pectate, benzenedicarboxylate, glutarate, hydroxymaleate, hydroxybenzoate, 3-hydroxy-2-naphthoate, 3-phenylpropionate, isobutyrate, pivalate, picrate, stearate, 2,2-dichloroacetate, acylated amino-acid salt, alginate, 4-acetamidobenzene sulfonate, decanoate, cholate, caprylate, pelargonate, cyclamate, phthalate, hydrochloride cysteine salt, sorbate, pamoate, hydrochloride glycinate, naphthalenedisulfonate, xylene sulfonate, dihydrochloride cystine salt, undecanoate, poly(vinylsulfonate), sulfosalicylate, phenylbutyrate, 4-hydroxybutyrate, poly(vinylsulfate), naphthalene-1l-sulfonate, naphthalene-2-sulfonate, valerate or a combination thereof.

In some embodiments, the acid addition salt provided herein is hydrochloride crystal-I of compound (I), which is characterized by an X-ray powder diffraction pattern comprising peaks expressed as 2θ at 3.68±0.2°, 10.88±0.2°, 17.30±0.2°, 22.20±0.2°, 26.67±0.2°.

In some embodiments, the acid addition salt provided herein is hydrochloride crystal-I of compound (I), which is characterized by an X-ray powder diffraction pattern comprising peaks expressed as 2θ at 3.68±0.2°, 10.88±0.2°, 11.53±0.2°, 12.43±0.2°, 17.30±0.2°, 17.65±0.2°, 19.43±0.2°, 21.83±0.2°, 22.20±0.2°, 22.90±0.2°, 25.51±0.2°, 26.67±0.2°.

In some embodiments, the acid addition salt provided herein is hydrochloride crystal-I of compound (I), which is characterized by an X-ray powder diffraction pattern comprising peaks expressed as 2θ at 3.68±0.2°, 7.25±0.2°, 10.88±0.2°, 11.53±0.2°, 12.43±0.2°, 12.74±0.2°, 13.63±0.2°, 14.47±0.2°, 14.77±0.2°, 15.23±0.2°, 16.82±0.2°, 17.30±0.2°, 17.65±0.2°, 18.16±0.2°, 19.43±0.2°, 20.19±0.2°, 21.41±0.2°, 21.83±0.2°, 22.20±0.2°, 22.90±0.2°, 23.28±0.2°, 23.79±0.2°, 24.13±0.2°, 24.64±0.2°, 24.99±0.2°, 25.51±0.2°, 25.97±0.2°, 26.67±0.2°, 27.30±0.2°, 27.73±0.2°, 28.86±0.2°, 29.33±0.2°, 29.88±0.2°, 31.02±0.2°, 31.81±0.2°, 32.39±0.2°, 32.83±0.2°, 34.05±0.2°, 34.48±0.2°, 35.69±0.2°, 36.56±0.2°, 37.07±0.2°, 37.83±0.2°.

In some embodiments, the acid addition salt provided herein is hydrochloride crystal-I of compound (I), which is characterized by an X-ray powder diffraction pattern substantially as shown in FIG. 1.

In some embodiments, the acid addition salt provided herein is hydrochloride crystal-I of compound (I), which is characterized by a Fourier transform infrared spectrogram comprising absorption peaks at 606, 656, 721, 756, 819, 878, 911, 964, 981, 1028, 1078, 1101, 1117, 1153, 1166, 1198, 1215, 1265, 1290, 1343, 1366, 1397, 1435, 1455, 1464, 1512, 1538, 1592, 1616, 1633, 1665, 1694, 1738, 1822, 1957, 2342, 2355, 2555, 2724, 2754, 2857, 2930, 2956, 3024, 3046, 3183, 3256, 3324, 3374, 3419, 3432, 3453, 3459, 3479, 3493 and 3500 cm$^{-1}$; the absorption peak has an error margin at ±2 cm$^{-1}$.

In some embodiments, the acid addition salt provided herein is hydrochloride crystal-I of compound (I), which is characterized by a Fourier transform infrared spectrogram substantially as shown in FIG. 2.

In some embodiments, the acid addition salt provided herein is hydrochloride crystal-II of compound (I), which is characterized by an X-ray powder diffraction pattern comprising peaks expressed as 2θ at 6.12±0.2°, 8.83±0.2°, 15.56±0.2°, 19.69±0.2°, 25.24±0.2°, 26.35±0.2°.

In some embodiments, the acid addition salt provided herein is hydrochloride crystal-II of compound (I), which is characterized by an X-ray powder diffraction pattern comprising peaks expressed as 2θ at 6.12±0.2°, 8.83±0.2°, 12.27±0.2°, 13.97±0.2°, 15.56±0.2°, 16.51±0.2°, 17.24±0.2°, 18.48±0.2°, 19.69±0.2°, 22.68±0.2°, 25.24±0.2°, 26.35±0.2°.

In some embodiments, the acid addition salt provided herein is hydrochloride crystal-II of compound (I), which is characterized by an X-ray powder diffraction pattern comprising peaks expressed as 2θ at 6.12±0.2°, 8.83±0.2°, 12.27±0.2°, 13.54±0.2°, 13.80±0.2°, 13.97±0.2°, 15.56±0.2°, 16.51±0.2°, 17.24±0.2°, 18.48±0.2°, 19.69±0.2°, 21.81±0.2°, 22.68±0.2°, 23.80±0.2°, 24.70±0.2°, 25.24±0.2°, 25.72±0.2°, 26.35±0.2°, 26.66±0.2°, 27.17±0.2°, 27.50±0.2°, 28.12±0.2°, 29.03±0.2°, 30.43±0.2°, 31.03±0.2°, 31.56±0.2°, 37.58±0.2°.

In some embodiments, the acid addition salt provided herein is hydrochloride crystal-II of compound (I), which is characterized by an X-ray powder diffraction pattern substantially as shown in FIG. 3.

In some embodiments, the acid addition salt provided herein is hydrochloride crystal-II of compound (I), which is characterized by a Fourier transform infrared spectrogram comprising absorption peaks at 667, 727, 757, 882, 969, 1026, 1039, 1081, 1109, 1159, 1199, 1291, 1365, 1396, 1439, 1457, 1478, 1509, 1545, 1593, 1611, 1666, 1729, 2524, 2550, 2581, 2684, 2871, 2934, 2955, 3010, 3257 and 3377 cm$^{-1}$, the absorption peak has an error margin at ±2 cm$^{-1}$.

In some embodiments, the acid addition salt provided herein is hydrochloride crystal-II of compound (I), which is characterized by a Fourier transform infrared spectrogram substantially as shown in FIG. 4.

In some embodiments, the acid addition salt provided herein is hydrochloride crystal-III of compound (I), which is characterized by an X-ray powder diffraction pattern comprising peaks expressed as 2θ at 3.46±0.2°, 10.25±0.2°, 13.62±0.2°, 17.26±0.2°.

In some embodiments, the acid addition salt provided herein is hydrochloride crystal-III of compound (I), which is characterized by an X-ray powder diffraction pattern comprising peaks expressed as 2θ at 3.46±0.2°, 10.25±0.2°, 13.62±0.2°, 17.26±0.2°, 20.56±0.2°, 24.10±0.2°, 26.44±0.2°, 26.66±0.2°, 27.35±0.2°.

In some embodiments, the acid addition salt provided herein is hydrochloride crystal-III of compound (I), which is characterized by an X-ray powder diffraction pattern comprising peaks expressed as 2θ at 3.46±0.2°, 6.80±0.2°, 10.25±0.2°, 11.51±0.2°, 11.93±0.2°, 12.77±0.2°, 13.62±0.2°, 14.77±0.2°, 17.26±0.2°, 18.95±0.2°, 19.83±0.2°, 20.56±0.2°, 21.64±0.2°, 22.57±0.2°, 23.09±0.2°, 24.10±0.2°, 26.44±0.2°, 26.66±0.2°, 27.35±0.2°, 28.41±0.2°, 29.09±0.2°, 30.50±0.2°, 31.67±0.2°, 34.16±0.2°, 37.13±0.2°, 39.38±0.2°.

In some embodiments, the acid addition salt provided herein is hydrochloride crystal-III of compound (I), which is characterized by an X-ray powder diffraction pattern substantially as shown in FIG. 12.

In some embodiments, the acid addition salt provided herein is sulfate crystal-I of compound (I), which is characterized by an X-ray powder diffraction pattern comprising peaks expressed as 2θ at 3.35±0.2°, 6.61±0.2°, 16.50±0.2°, 21.43±0.2°.

In some embodiments, the acid addition salt provided herein is sulfate crystal-I of compound (I), which is characterized by an X-ray powder diffraction pattern comprising peaks expressed as 2θ at 3.35±0.2°, 6.61±0.2°, 13.20±0.2°, 16.50±0.2°, 19.03±0.2°, 21.43±0.2°, 23.19±0.2°.

In some embodiments, the acid addition salt provided herein is sulfate crystal-I of compound (I), which is characterized by has an X-ray powder diffraction pattern comprising peaks expressed as 2θ at 3.35±0.2°, 6.61±0.2°, 7.89±0.2°, 9.90±0.2°, 10.45±0.2°, 12.74±0.2°, 13.20±0.2°, 14.86±0.2°, 15.22±0.2°, 16.50±0.2°, 16.87±0.2°, 17.30±0.2°, 18.40±0.2°, 19.03±0.2°, 19.43±0.2°, 19.65±0.2°, 20.56±0.2°, 20.87±0.2°, 21.43±0.2°, 21.74±0.2°, 23.19±0.2°, 23.45±0.2°, 23.80±0.2°, 24.60±0.2°, 25.29±0.2°, 25.90±0.2°, 26.07±0.2°, 26.40±0.2°, 27.26±0.2°, 28.22±0.2°, 28.47±0.2°, 30.82±0.2°, 31.75±0.2°, 33.80±0.2°, 34.55±0.2°, 36.77±0.2°, 37.30±0.2°, 39.02±0.2°.

In some embodiments, the acid addition salt provided herein is sulfate crystal-I of compound (I), which is characterized by an X-ray powder diffraction pattern substantially as shown in FIG. 5.

In some embodiments, the acid addition salt provided herein is sulfate amorphism of compound (I), which is characterized by an X-ray powder diffraction pattern substantially as shown in FIG. 6.

In some embodiments, the acid addition salt provided herein is tosilate crystal-I of compound (I), which is characterized by an X-ray powder diffraction pattern comprising peaks expressed as 2θ at 6.55±0.2°, 13.74±0.2°, 20.08±0.2°, 21.32±0.2°, 22.17±0.2°, 22.99±0.2°.

In some embodiments, the acid addition salt provided herein is tosilate crystal-I of compound (I), which is characterized by an X-ray powder diffraction pattern comprising peaks expressed as 2θ at 6.55±0.2°, 13.74±0.2°, 13.96±0.2°, 17.18±0.2°, 17.44±0.2°, 19.83±0.2°, 20.08±0.2°, 20.31±0.2°, 21.32±0.2°, 22.17±0.2°, 22.99±0.2°, 26.83±0.2°.

In some embodiments, the acid addition salt provided herein is tosilate crystal-I of compound (I), which is characterized by an X-ray powder diffraction pattern comprising peaks expressed as 2θ at 6.55±0.2°, 8.18±0.2°, 8.68±0.2°, 9.37±0.2°, 9.60±0.2°, 9.97±0.2°, 10.80±0.2°, 11.05±0.2°, 12.80±0.2°, 13.18±0.2°, 13.74±0.2°, 13.96±0.2°, 15.48±0.2°, 16.41±0.2°, 17.18±0.2°, 17.44±0.2°, 17.87±0.2°, 18.18±0.2°, 18.97±0.2°, 19.83±0.2°, 20.08±0.2°, 20.31±0.2°, 20.95±0.2°, 21.32±0.2°, 22.17±0.2°, 22.47±0.2°, 22.99±0.2°, 23.79±0.2°, 24.02±0.2°, 24.86±0.2°, 25.44±0.2°, 26.27±0.2°, 26.83±0.2°, 27.32±0.2°, 27.65±0.2°, 28.10±0.2°, 29.06±0.2°, 30.39±0.2°, 30.87±0.2°, 31.57±0.2°, 32.04±0.2°, 33.18±0.2°, 36.87±0.2°.

In some embodiments, the acid addition salt provided herein is tosilate crystal-I of compound (I), which is characterized by an X-ray powder diffraction pattern comprising peaks substantially as shown in FIG. 7.

In some embodiments, the acid addition salt provided herein is tosilate crystal-I of compound (I), which is characterized by a differential scanning calorimetry thermogram comprising an endothermic peak at 231.51° C.±3° C.

In some embodiments, the acid addition salt provided herein is tosilate crystal-I of compound (I), which is characterized by a differential scanning calorimetry thermogram substantially as shown in FIG. 8.

In some embodiments, the acid addition salt provided herein is tosilate amorphism of compound (I), which is characterized by an X-ray powder diffraction pattern substantially as shown in FIG. 9.

In some embodiments, the acid addition salt provided herein is maleate crystal-I of compound (I), which is characterized by an X-ray powder diffraction pattern comprising peaks expressed as 2θ at 4.10±0.2°, 16.33±0.2°, 20.45±0.2°.

In some embodiments, the acid addition salt provided herein is maleate crystal-I of compound (I), which is characterized by an X-ray powder diffraction pattern comprising peaks expressed as 2θ at 4.10±0.2°, 8.16±0.2°, 16.33±0.2°, 17.72±0.2°, 20.45±0.2°, 21.58±0.2°, 24.63±0.2°.

In some embodiments, the acid addition salt provided herein is maleate crystal-I of compound (I), which is characterized by an X-ray powder diffraction pattern comprising peaks expressed as 2θ at 4.10±0.2°, 8.01±0.2°, 8.16±0.2°, 12.23±0.2°, 13.94±0.2°, 14.31±0.2°, 15.32±0.2°, 16.33±0.2°, 16.82±0.2°, 17.72±0.2°, 18.38±0.2°, 18.39±0.2°, 19.14±0.2°, 19.77±0.2°, 20.45±0.2°, 20.95±0.2°, 21.58±0.2°, 22.34±0.2°, 23.87±0.2°, 24.63±0.2°, 25.56±0.2°, 26.43±0.2°, 27.51±0.2°, 28.24±0.2°, 28.78±0.2°, 29.62±0.2°, 30.13±0.2°, 30.93±0.2°, 33.01±0.2°, 35.58±0.2°, 37.37±0.2°.

In some embodiments, the acid addition salt provided herein is maleate crystal-I of compound (I), which is characterized by an X-ray powder diffraction pattern substantially as shown in FIG. 10.

In some embodiments, the acid addition salt provided herein is maleate crystal-I of compound (I), which is characterized by a differential scanning calorimetry thermogram comprising an endothermic peak at 116.28° C.±3° C.

In some embodiments, the acid addition salt provided herein is maleate crystal-I of compound (I), which is characterized by a differential scanning calorimetry thermogram substantially as shown in FIG. 11.

In one aspect, the present invention also provides a pharmaceutical composition comprising any one acid addition salt of compound (I) or a combination thereof; optionally, the pharmaceutical composition further comprises a pharmaceutically acceptable carrier, excipient, diluent, adjuvant or a combination thereof. In some embodiments, the acid addition salt in the pharmaceutical composition provided herein can be in any one kind crystal-form, specifically can be in any crystalline form, amorphism or a combination thereof. In some embodiments, the pharmaceutical composition provided herein comprises any one acid addition salt of compound (I), or any one kind crystalline form provided herein or amorphism, or any one combination of the salt, crystalline form or amorphism.

In other aspect, the present invention also provides use of the acid addition salt of compound (I) or a combination thereof or the pharmaceutical composition in the manufacture of a medicament, wherein the medicament is used for preventing, treating or lessening a tissue or organ fibrosis disorder in a human or animal; furthermore, the use comprises administering a therapeutically effective amount of the acid addition salt provided herein or the pharmaceutical composition to a patient or animal.

In some embodiments, the tissue or organ fibrosis disorder provided herein is renal interstitial fibrosis, glomerulosclerosis, liver fibrosis, pulmonary fibrosis, peritoneal fibrosis, myocardial fibrosis, dermatofibrosis, post-surgery adhesions, benign prostatic hypertrophy, skeletal muscle fibrosis, dermatosclerosis, multiple sclerosis, pancreatic fibrosis, liver cirrhosis, myosarcoma, neurofibroma, pulmonary interstitial fibrosis, diabetic nephropathy, alzheimer disease or vascular fibrosis.

In some other embodiments, the pulmonary fibrosis provided herein includes idiopathic pulmonary fibrosis (IPF).

In some other embodiments, the post-surgery adhesions provided herein is scar healing.

The present invention also relates to use of the acid addition salt of compound (I) or a combination thereof or the pharmaceutical composition in the manufacture of a medicament, wherein the medicament is used for preventing, treating or lessening diabetic nephropathy or alzheimer disease in a patient.

In other aspect, the present invention relates to a method of preventing, treating or lessening a tissue or organ fibrosis disorder in a patient, comprising administering a therapeutically effective amount of the acid addition salt provided herein or a combination thereof or the pharmaceutical composition to a patient.

In some embodiments, the tissue or organ fibrosis disorder provided herein is renal interstitial fibrosis, glomerulosclerosis, liver fibrosis, pulmonary fibrosis, peritoneal fibrosis, myocardial fibrosis, dermatofibrosis, post-surgery adhesions, benign prostatic hypertrophy, skeletal muscle fibrosis, dermatosclerosis, multiple sclerosis, pancreatic fibrosis, liver cirrhosis, myosarcoma, neurofibroma, pulmonary interstitial fibrosis, diabetic nephropathy, alzheimer disease or vascular fibrosis.

In some other embodiments, the pulmonary fibrosis provided herein includes idiopathic pulmonary fibrosis (IPF).

In some other embodiments, the post-surgery adhesions provided herein is scar healing.

The present invention in other aspect relates to the acid addition salt of compound (I) or a combination thereof or the pharmaceutical composition for use in preventing, treating or lessening a tissue or organ fibrosis disorder.

In some embodiments, the tissue or organ fibrosis disorder provided herein is renal interstitial fibrosis, glomerulosclerosis, liver fibrosis, pulmonary fibrosis, peritoneal fibrosis, myocardial fibrosis, dermatofibrosis, post-surgery adhesions, benign prostatic hypertrophy, skeletal muscle fibrosis, dermatosclerosis, multiple sclerosis, pancreatic fibrosis, liver cirrhosis, myosarcoma, neurofibroma, pulmonary interstitial fibrosis, diabetic nephropathy, alzheimer disease or vascular fibrosis.

In some other embodiments, the pulmonary fibrosis provided herein includes idiopathic pulmonary fibrosis (IPF).

In some other embodiments, the post-surgery adhesions provided herein is scar healing.

In other aspect, the present invention also relates to a method of preparing the acid addition salt of compound (I) provided herein and a crystalline form thereof.

The crystalline forms of the acid addition salt provided herein can be prepared by some common methods, wherein some crystalline forms provided herein also can be obtained by crystal transformation.

The amorphism provided herein can be obtained by spray drying. The yield of the amorphism obtained by spray drying is affected by some factors such as the air intake temperature or air outlet temperature of the instrument, or the system pressure during the spray process and so on, and the air intake temperature or air outlet temperature of the instrument, or the system pressure during the spray process relates to instrument model, the used solvent and other factors.

The solvent used in the method for preparing the salt provided herein is not particularly restricted, any solvent is contained in the invention so long as it can dissolve the raw materials to a certain extent and do not impact properties of which. Additionally, many similar modifications in the art, substitutions to same object, or equivalent to solvent, solvent combination and the solvent combination with different proportions described in the invention, all are deemed to be included in the present invention. The optimal solvents used in any reaction step are provided herein.

The preparation experiment of the salt provided herein would be detailed in examples. Meanwhile, the present invention provides an activity test (such as pharmacokinetics test), solubility test, stability test and hygroscopicity test, etc. of the salt. It can be known from the results that the salts provided herein have a better biological activity (such as better pharmacokinetic properties), good solubility, high stability, and which are suitable for pharmacy.

Wherein the feature description of hygroscopicity and definition of weight gain of hygroscopicity (Chinese Pharmacopoeia 2015 edition appendix 9103 drug hygroscopicity guiding principles, experimental conditions: 25° C.±1° C., 80%±2% relative humidity) are described as followed table:

The Feature Description of Hygroscopicity and Definition of Weight Gain of Hygroscopicity

| hygroscopicity characteristics | weight gain of hygroscopicity |
|---|---|
| deliquescence | absorbing enough water and forming liquid |
| very hygroscopicity | no less than 15% |
| hygroscopicity | less than 15% but no less than 2% |
| sparingly hygroscopicity | less than 2% but no less than 0.2% |
| no or almost no hygroscopicity | less than 0.2% |

The salt provided herein is not easy to be influenced by high humidity to deliquesce, the property is convenience for long period storage.

The salt and the pharmaceutical composition provided herein are less toxic. The inventors found that the hydrochloride salt or the pharmaceutical composition thereof is less toxic in dogs, such as vomiting and the like.

Definitions and General Terminology

Unless otherwise defined, all technical and scientific terms used herein have the same meaning as commonly understood by one of ordinary skill in the art to which this invention belongs. All patents and publications referred to herein are incorporated by reference in their entirety. Although any methods and materials similar or equivalent to those described herein can be used in the practice or testing of the present invention, the preferred methods, devices, and materials are now described.

"Pharmaceutically acceptable acid addition salt" refers to a salt formed from compound (I) of the invention and pharmaceutically acceptable nontoxic acid, including but not limited to various organic acid salts and inorganic acid salts described herein.

"Acid addition salt of compound (I)" refers to a salt formed from compound (I) (free base) and one of various suitable organic acid salts and inorganic acid salts, including but not limited to hydrochloride, hydrobromide, sulfate, maleate, benzene sulfonate, tosilate, naphthalenesulfonate, oxalate, mesylate, and so on described herein. Wherein the "acid addition salt of compound (I)" includes amorphous form or crystalline form, includes solvate (for example, hydrate), and also includes polymorphism of the salt. For example, hydrochloride of compound (I) includes amorphous form, various crystalline forms, various solvates, various hydrates, and also polymorphism of the salt.

"Crystalline" or "crystal form" refers to a solid having a highly regular chemical structure, includes, but are not limited to, single- and multiple-component crystals, and/or polymorphic form of compound, solvate, hydrate, clathrate, cocrystal, salt, solvate of salt, hydrate of salt. Crystalline forms of a substance can be obtained by a number of methods, as known in the art. Such methods include, but are not limited to, melt crystallization, melt cooling, solvent crystallization, crystallization in confined spaces such as, e.g., in nanopores or capillaries, crystallization on surfaces or templates such as, e.g., on polymers, crystallization in the presence of additives, such as, e.g., co-crystal counter-molecules, desolvation, dehydration, rapid evaporation, rapid cooling, slow cooling, vapor diffusion, sublimation, reaction crystallization, antisolvent addition, grinding and solvent-drop grinding.

"Amorphism" or "amorphous form" refers to substance forming by particle (such as molecule, atom, ion) arranged in no periodic in three-dimensional space, which is characterized by a diffused X-ray powder diffraction pattern with no sharp peaks. Amorphism is a special physical form of solid substance, the ordered structural characteristics in a part of amorphous substance imply there are innumerable links between amorphous substance and crystal substance. Amorphous substance can be obtained through many methods as known in the art. These methods include, but are not limited to, rapid freezing method, anti-solvent flocculence method, ball-milling method, spray drying method, freeze-drying method, wet granulating method and solid dispersion technique, and the like.

The term "solvent", means a substance, typically a liquid, that is capable of completely or partially dissolving another substance, typically a solid. "Solvent," as used herein, include but are not limited to water, acetic acid, acetone, acetonitrile, benzene, chloroform, carbon tetrachloride, dichloromethane, dimethylsulfoxide, 1,4-dioxane, ethanol, ethyl acetate, butanol, tert-butanol, N,N-dimethylacetamide, N,N-dimethylformamide, formamide, formic acid, heptane, hexane, isopropanol, methanol, methyl ethyl ketone, mesitylene, nitromethane, polyethylene glycol, propanol, pyridine, tetrahydrofuran, toluene, xylene, mixtures thereof and the like.

The term "anti-solvent" refers to a fluid which promotes precipitation from the solvent of the product (or a precursor for the product). The anti-solvent may comprise a cold gas, or a fluid promoting the precipitation via a chemical reaction, or a fluid which decreases the solubility of the product in the solvent; it may be the same liquid as the solvent but at a different temperature or it may be a different liquid from the solvent.

The term "solvate," as used herein, means having on a surface, in a lattice or on a surface and in a lattice, a solvent such as water, acetic acid, acetone, acetonitrile, benzene, chloroform, carbon tetrachloride, dichloromethane, dimethylsulfoxide, 1,4-dioxane, ethanol, ethyl acetate, butanol, tert-butanol, N,N-dimethylacetamide, N,N-dimethylformamide, formamide, formic acid, heptane, hexane, isopropanol, methanol, methyl ethyl ketone, 1-methyl-2-pyrrolidinone, mesitylene, nitromethane, polyethylene glycol, propanol, pyridine, tetrahydrofuran, toluene, xylene, mixtures thereof and the like. A specific example of a solvate is a hydrate, wherein the solvent on the surface, in the lattice or on the surface and in the lattice, is water. Hydrates may or may not have solvents other than water on the surface, in the lattice or on the surface and in the lattice of a substance.

Crystalline form or amorphism can be identified through multiple technological means, such as X-ray powder diffraction (XRPD), infrared spectroscopy (IR), melting point method, differential scanning calorimetry (DSC), thermogravimetry analysis (TGA), nuclear magnetic resonance method, Raman spectroscopy, X-ray single crystal diffraction, solution calorimetry, scanning electron microscope (SEM), quantitative analysis, solubility, dissolution velocity, etc.

Some information such as change in crystalline form, crystallinity, crystal structure state, etc., can be obtained through detection of X-ray powder diffraction (XRPD) which is a common method used for identifying crystalline form. The peak position of XRPD pattern mainly depends on the crystal structure, which is relatively insensitive to experimental details, and the relative peak height depends on many factors related to sample preparation and the geometry of the instrument. Thus, in some embodiments, the crystalline form disclosed herein is characterized by an X-ray powder diffraction pattern having some peaks in certain positions, which is substantially the same as the XRPD pattern provided in appended figures of the present invention. Meanwhile, the measurement of 2θ in XRPD pattern could have some experimental errors, for example the measurements of 2θ in XRPD pattern could be slightly different because of different instruments and different samples. Therefore, the value of 2θ is not absolute. According to the state of the instrument for the experiment, the error margin in 2θ of the characteristic peaks is ±0.2°.

Differential scanning calorimetry (DSC) is a technology used for measuring the energy difference between a sample and a inert reference compound (usually $\alpha\text{-Al}_2\text{O}_3$) as a function of temperature, which is performed through constant heating or cooling under program control. The endothermic peak height of DSC thermogram depends on many factors related to sample preparation and the geometry of the instrument, and the peak position is relatively insensitive to experimental details. Thus, in some embodiments, the crystalline form disclosed herein is characterized by a DSC thermogram having some peaks in certain positions, which is substantially the same as the DSC thermogram provided in appended figures of the present invention. Meanwhile, a DSC thermogram could have some experimental errors, for example the peak position and the peak value in the DSC thermogram could be slightly different because of different instruments and different samples. Therefore, the peak position and the peak value in the DSC thermogram are not absolute. According to the state of the instrument for the experiment disclosed herein, the error margin in the endothermic peaks is ±3° C.

Differential scanning calorimetry (DSC) also is used for detection and analysis whether there is crystal transformation or mixed grain phenomenon in crystalline form.

Solids having same chemical composition usually form polymorphs, or called variant, having different crystal structures under different thermodynamic conditions, this phenomenon is called polymorphism or polyphase. When conditions of temperature and pressure change, there will be a change between variants, which is called crystal transition. The property of crystalline forms changed largely such as mechanics, electrics, magnetics because of crystal transition. The crystal transition process could be observed in differential scanning calorimetry (DSC) thermogram when the transition temperature within a measurable range, which is characterized by the DSC thermogram having a exothermic peak reflecting this transformation and two or more endothermic peaks which respectively are characteristic endothermic peaks of different crystalline forms before and after the transformation.

Thermogravimetric analysis (TGA) is a technology for determining the quantitative change of a substance as a function of temperature under program control, which suitable for detecting the process of the solvent loss in the crystal or sublimation and dissociation of the sample, and the condition of crystal water and crystal solvent contained in crystal may be speculated through analysis of the detection results. The quality change described in TGA curve depends on many factors related to sample preparation and instrument; and the quantitative change detected by TGA could be slightly different because of different instruments and different samples. The amorphous form of the invention is characterized that the weight loss of TGA detection is ranged from 1.75% to 4.10%. According to the state of the instrument for the experiment disclosed herein, the error margin of the quality change is ±0.1%.

Raman spectroscopy is a spectrophotometry used for studying vibration mode and rotation mode of molecules and other low frequency mode in one system. Different spatial structures of the same molecule have different Raman activities. Therefore, Raman spectroscopy could be used for determining and identifying crystalline form or amorphism. The peak position of Raman spectroscopy mainly relates to the structure of substances, which is relatively insensitive to experimental details, and the peak intensity depends on factors such as sample preparation and instrument. Thus, the crystalline form or amorphism disclosed herein is characterized by a Raman spectrogram having characteristic peaks in certain position, which is substantially the same as the Raman spectrogram provided in appended figures of the present invention. Meanwhile, a Raman spectrogram could have some experimental errors, the peak position and the peak value in the Raman spectrogram could be slightly different because of different instruments and different samples. Therefore, the peak position and the peak value in the Raman spectrogram are not absolute. According to the state of the instrument for the experiment disclosed herein, the error margin of the absorption peaks is ±2 $cm^{-1}$.

The bond length and the bond angle of certain chemical bonds in different spatial structures of the same molecule are different, which leads to different energy levels of vibration-rotational transition of the molecule and differences in the main characteristics of the corresponding infrared spectroscopy such as frequency of absorption band, peak shape, peak position, peak intensity, and so on, thus, infrared spectroscopy can be used in a research of drug polymorphism. The crystalline form or amorphism disclosed herein is characterized by a Fourier infrared (FT-IR) spectrogram having characteristic peaks in certain position, which is substantially the same as the Fourier infrared spectrogram provided in appended figures of the present invention. Meanwhile, a Raman spectrogram could have some experimental errors, the peak position and the peak value in the Raman spectrogram could be slightly different because of different instruments and different samples. Therefore, the peak position and the peak value in the Raman spectrogram are not absolute. According to the state of the instrument for the experiment disclosed herein, the error margin of the absorption peaks is ±2 $cm^{-1}$.

As used herein, the value of 2θ in X-ray powder diffraction (XRPD) pattern is in (°) degrees.

The term "substantially as shown in figure" refers to an X-ray powder diffraction (XRPD) pattern, or a differential scanning calorimetry (DSC) thermogram, or a Raman spectrogram, or a infrared spectrogram has at least 50%, at least 60%, at least 70%, at least 80%, at least 90%, at least 95%, or at least 99% of the peaks shown in the figure.

When referring to a spectrum and/or data presented in a figure, the term "peak" refers to a feature would not be attributed to background noise that one skilled in the art would recognize.

The various novel crystalline forms of the acid addition salt of 3-(4-(dihexylamino)-3-fluorophenyl)-2,6-dimethylpyrimidin-4(3H)-one referred herein are exist in a substantially pure crystalline forms.

The amorphism of the acid addition salt of 3-(4-(dihexylamino)-3-fluorophenyl)-2,6-dimethylpyrimidin-4(3H)-one referred herein is prepared by spray drying.

The term "substantially pure" refers to a crystalline form that is substantially free of one or more other crystalline forms, i.e., the crystalline form has a purity of at least about 80%, at least about 85%, at least about 90%, at least about 93%, at least about 95%, at least about 98%, at least about 99%, at least about 99.5%, at least about 99.6%, at least about 99.7%, at least about 99.8%, or at least about 99.9%; or the crystalline form comprises other crystalline forms, and the percentage of the other crystalline forms in total volume or total weight is less than 20%, less than 10%, less than 5%, less than 3%, less than 1%, less than 0.5%, less than 0.1%, or less than 0.01%.

The term "substantially free" refers to the percentage of one or more other crystalline forms in total volume or total weight is less than 20%, less than 10%, less than 5%, less than 4%, less than 3%, less than 2%, less than 1%, less than 0.5%, less than 0.1%, or less than 0.01%.

The term "relative intensity" (or "relative height") in XRPD pattern refers to the intensity of a peak with respect to the intensity of the strongest peak in the X-ray powder diffraction (XRPD) pattern which is regarded as 100%.

As used in the context of the present invention, regardless of whether the word "about" is used, which means within 10%, suitably within 5% and particularly within 1% of a given value or range. Alternatively, the term "about" means within an acceptable standard error of the mean for those of ordinary skill in the art. Whenever a number having a value N is disclosed, any number having the value within N+/−1%, N+/−2%, N+/−3%, N+/−5%, N+/−7%, N+/−8% or N+/−10% is specifically disclosed, wherein "+/−" refers to plus or minus.

As used herein, "room temperature" refers to a temperature from about 10° C. to about 40° C. In some embodiments, "room temperature" is from about 20° C. to about 30° C.; in other embodiments, "room temperature" is at 20° C., 22.5° C., 25° C., 27.5° C., and so on.

Composition, Formulation, Administration and Uses of the Acid Addition Salts of the Compound of the Invention The characteristics of the pharmaceutical composition of the invention include acid addition salts of compound (I) and pharmaceutically acceptable carrier, adjuvant, or excipient. The amount of the acid addition salt of the compound in the pharmaceutical composition of the invention can effectively and detectably treat or lessen a tissue or organ fibrosis disorder.

As described above, the pharmaceutically acceptable compositions disclosed herein further comprise a pharmaceutically acceptable carrier, an adjuvant, or a vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired.

As described in following references: In Remington: Troy et al., Remington: The Science and Practice of Pharmacy, 21st ed., 2005, Lippincott Williams & Wilkins, Philadelphia, and Swarbrick et al., Encyclopedia of Pharmaceutical Technology, eds. 1988-1999, Marcel Dekker, New York, both of which are herein incorporated by reference in their entireties, discloses various carriers used in formulating pharmaceutically acceptable compositions and known techniques for the preparation thereof. Except insofar as any conventional carrier medium incompatible with the compounds disclosed herein, such as by producing any undesirable biological effect or otherwise interacting in a deleterious manner with any other components of the pharmaceutically acceptable composition, its use is contemplated to be within the scope of this invention.

Some non-limiting examples of materials which can serve as pharmaceutically acceptable carriers include ion exchangers; aluminium; aluminum stearate; lecithin; serum proteins such as human serum albumin; buffer substances such as phosphates; glycine; sorbic acid; potassium sorbate; partial glyceride mixtures of saturated vegetable fatty acids; water; salts or electrolytes such as protamine sulfate, disodium hydrogen phosphate, potassium hydrogen phosphate, sodium chloride and zinc salts; colloidal silica; magnesium trisilicate; polyvinyl pyrrolidone; polyacrylates; waxes; polyethylene-polyoxypropylene-block polymers; wool fat; sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols such as propylene glycol and polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol; and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants.

The compositions disclosed herein may be capsules, tablets, pills, powders, granules and suspension in water or solution; and which may be administered by the following method: orally, parenterally, by inhalation spray, topically, rectally, nasally, buccally, vaginally or via an implanted reservoir.

Orally administration can be in the following administrative forms: tablets, pellets, capsules, dispensable powders, particles or suspensions, syrup, and elixirs. Alternatively, it can be administered by external use in the form of ointment, gel, drug-containing rubber cement, etc.

The compositions of the invention can be administered parenterally in the form of sterile injectable solution or suspension, and also may be administered parenterally or intraperitoneally. Solutions or suspensions of these active compounds as a free base or pharmacologically acceptable salt can be prepared in water suitably mixed with a surfactant such as hydroxypropylcellulose, polyvinylpyrrolidone. Dispersions can also be prepared in glycerol, liquid, polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringe ability exits. It must be stable under conditions of manufacture and storage and must be preserved against the contaminating action of microorganisms such as bacterium and fungi. The carrier can be a solvent or dispersion medium containing, for example, water, ethanol (e.g., glycerol, propylene glycol and liquid polyethylene glycol), suitable mixtures thereof, and vegetable oil.

One may administer the compound or the salt or the pharmaceutical composition disclosed herein in a local rather than systemic manner. For example, via injection of the compound directly into an organ, often in a depot or sustained release formulation. Furthermore, one may administer pharmaceutical composition containing a compound of the invention in a targeted drug delivery system, for example, in a liposome coated with organ-specific antibody. The liposomes will be targeted to and taken up selectively by the organ. In addition, pharmaceutical compositions containing a compound of the invention may be provided in the form of a rapid release formulation, in the form of an extended release formulation, or in the form of an intermediate release formulation.

For administration by inhalation, the compound or the salt thereof of the invention may be in a form as an aerosol, a mist or a powder. Pharmaceutical compositions of the compound or salts thereof of the invention may be conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Capsules and cartridges, such as, by way of example only, gelatin for use in an inhaler or insufflator may be formulated containing a powder mix of the compound and a suitable powder base such as lactose or starch.

The compound or salts thereof of the invention may also be formulated in rectal compositions such as enemas, rectal gels, rectal foams, rectal aerosols, suppositories, jelly suppositories, or retention enemas, containing conventional suppository bases such as cocoa butter or other glycerides, as well as synthetic polymers such as polyvinylpyrrolidone, PEG, and the like. In suppository forms of the compositions, a low-melting wax such as, but not limited to, a mixture of fatty acid glycerides, optionally in combination with cocoa butter is first melted.

In addition, the compound or salts thereof also can be combined with other drugs for treating fibrosis. The other drugs comprise but are not limited to, Ivacaftor, Roflumilast, Pirfenidone, nintedanib, Miglustat, Losartan, interferon, Arafa-streptodornase, Veldona, ataluren, cortical hormone, amethopterin, Tacrolimus, and so on.

Pharmaceutical compositions may be formulated in conventional manner using one or more physiologically acceptable carriers comprising excipients and auxiliaries which facilitate processing of the active compounds into preparations which may be used pharmaceutically. Proper formulation is dependent upon the route of administration chosen. Any of the well-known techniques, carriers, and excipients may be used as suitable and as understood in the art. Pharmaceutical compositions comprising a compound of the invention may be manufactured in a conventional manner, such as, by way of example only, by means of conventional mixing, dissolving, granulating, dragee-making, levigating, emulsifying, encapsulating, entrapping or compression processes. Pharmaceutical compositions containing a compound of the invention may be administered in therapeutically effective amounts as pharmaceutical compositions by any conventional form and route known in the art including, but not limited to: intravenous, oral, rectal, aerosol, parenteral, ophthalmic, pulmonary, transdermal, vaginal, otic, nasal, and topical administration.

The pharmaceutical compositions will include at least one pharmaceutically acceptable carrier, diluent or excipient and the compound or salts thereof described herein as an active ingredient in free-acid or free-base form, or in a pharmaceutically acceptable salt form. In addition, the pharmaceutical compositions may include other medicinal or pharmaceutical agents, carriers, adjuvants, such as preserving, stabilizing, wetting or emulsifying agents, solution promoters, salts for regulating the osmotic pressure, and/or buffers. In addition, the pharmaceutical compositions may also contain other therapeutically valuable substances.

Methods for the preparation of compositions comprising the compounds described herein include formulating the compounds with one or more inert, pharmaceutically acceptable excipients or carriers to form a solid, semi-solid or liquid. Solid compositions include, but are not limited to, powders, tablets, dispersible granules, capsules, cachets, and suppositories. Liquid compositions include solutions in which a compound is dissolved, emulsions comprising a compound, or a solution containing liposomes, micelles, or nanoparticles comprising a compound as disclosed herein. Semi-solid compositions include, but are not limited to, gels, suspensions and creams. The compositions may be in liquid solutions or suspensions, solid forms suitable for solution or suspension in a liquid prior to use, or as emulsions. These compositions may also contain minor amounts of nontoxic, auxiliary substances, such as wetting or emulsifying agents, pH buffering agents, and so forth.

The compound or salts thereof disclosed herein are preferably formulated in dosage unit form for ease of administration and uniformity of dosage. The expression "dosage unit form" refers to a physically discrete unit of agent appropriate for the patient to be treated. It will be understood, however, that the total daily usage of the compound or salts thereof or pharmaceutical compositions disclosed herein will be decided by the attending physician within the scope of sound medical judgment. The specific effective dose level for any particular patient or organism will depend upon a variety of factors including the disorder being treated and the severity of the disorder; the activity of the specific compound or salts thereof employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts.

The effective dose of the active ingredient used can be varied with the compounds or salts thereof used, the mode of administration and the severity degree of the disease to be treated. However, satisfactory results can be obtained, when the compounds of the present invention were administered with the daily dose of about 0.25-1000 mg/kg animal weight; preferably, administered with 2-4 divided doses every day, or administered in the form of sustained release. For most of the large mammals, the total daily dose is about 1-100 mg/kg, preferably about 2-80 mg/kg. Dosage forms suitable for oral administration contain about 0.25-500 mg of the active compounds intimately mixed with a solid or liquid pharmaceutically acceptable carrier. The dose can be adjusted to provide the optimal therapeutic response. In addition, according to the urgent requirements of the treatment status, several divided doses can be administered daily or the dose can be reduced proportionally.

The compound or salts thereof, pharmaceutical compositions can be used effectively in preventing, managing, treating or lessening a tissue or organ fibrosis disorder in a patient, specifically for treating effectively renal interstitial fibrosis, glomerulosclerosis, liver fibrosis, pulmonary fibrosis, idiopathic pulmonary fibrosis, peritoneal fibrosis, myocardial fibrosis, dermatofibrosis, post-surgery adhesions, benign prostatic hypertrophy, skeletal muscle fibrosis, dermatosclerosis, multiple sclerosis, pancreatic fibrosis, liver cirrhosis, myosarcoma, neurofibroma, pulmonary interstitial fibrosis, diabetic nephropathy, alzheimer disease or vascular fibrosis

EXAMPLES

Figure 1:
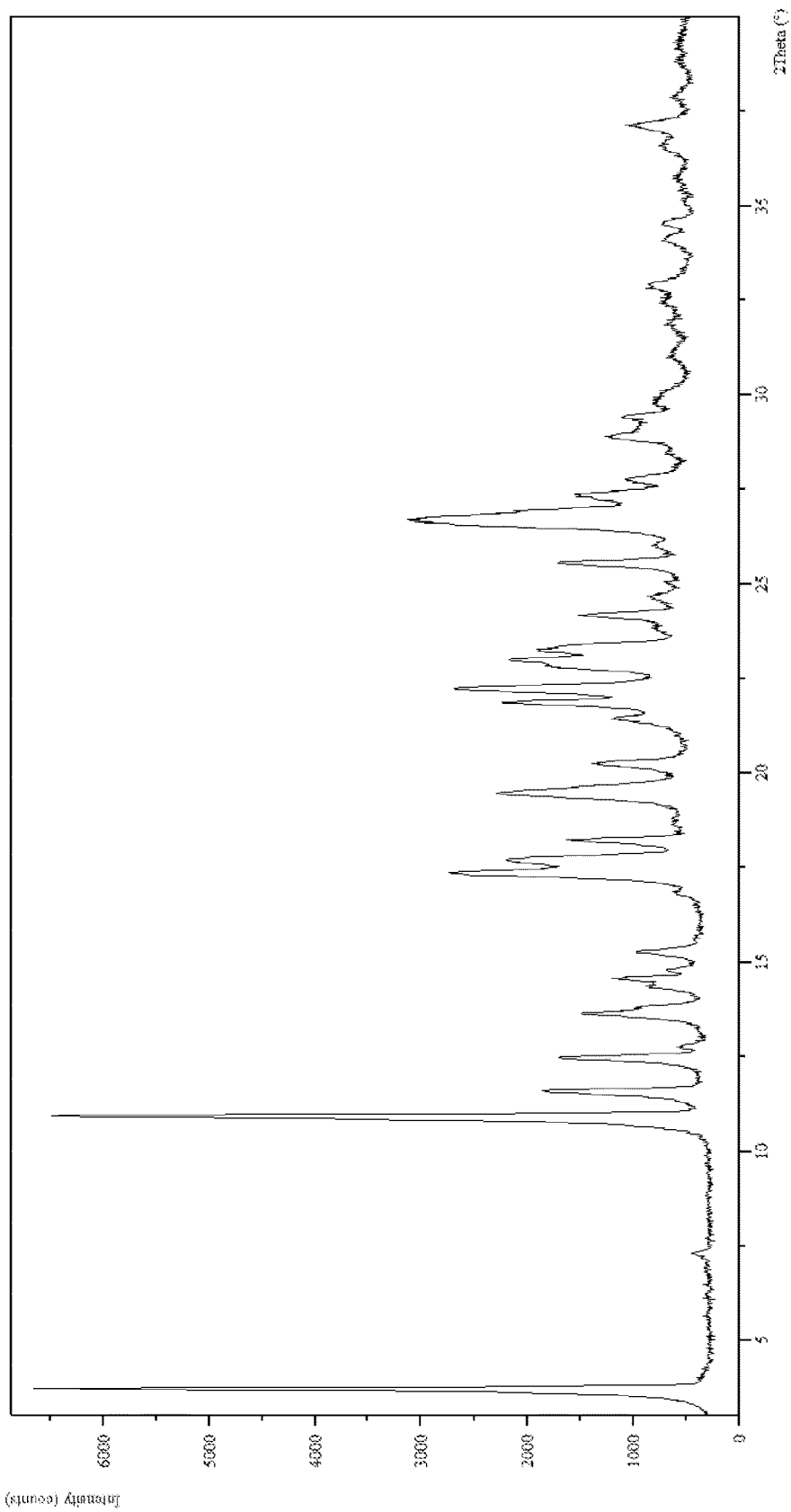
FIG. 1 shows that the X-ray powder diffraction pattern of hydrochloride crystal-I of the compound of formula (I)

The invention is illustrated further by the following examples, which are not be construed as limiting the invention in scope.

The X ray powder diffraction analysis method disclosed herein is: X-ray powder diffraction diagram was recorded on an Empyrean diffraction, using Cu-Kα radiation (45 KV, 40 mA). A thin layer was prepared from powder sample on the single-crystal silicon sample holder, and which was put on a rotary sample stage and, analyzed in the range from 3° to 400 with a 0.0168° step size. Data were collected by Data Collector software, and processed by HighScore Plus software, read by Data Viewer software.

The differential Scanning Calorimetry (DSC) analysis method disclosed herein is: Differential scanning calorimetry thermogram was recorded on a TA Q2000 module with a thermoanalysis controller. The data were processed and analyzed by using TA Instruments Thermal Solutions software. About 1-5 mg sample was weighed accurately in a special aluminium crucible with a lid, and heated using a linear heating device in 10° C./minute and analyzed from room temperature to about 300° C. DSC cabin was purged with dry nitrogen during use.

The Fourier transform infrared spectrum (FT-IR) analysis method disclosed is: Fourier transform infrared spectrogram was recorded on TENSOR27 Germanic Bruker infrared spectrometer. The data were collected and analyzed by OPUS software. KBr disk was prepared, the scan times is 16 times, the wave number range is from 4000 to 600 cm$^{-1}$, the resolution is 2 cm$^{-1}$ The solubility disclosed herein was measured by Aglient 1200 high performance liquid chromatograph VWD detector. The chromatographic column model is Waters Xbridge-C18 (4.6×150 mm, 5 μm). The detection wavelength was 266 nm, the flow rate was 1.0 mL/min, the column temperature was 35° C., the mobile phase A is acetonitrile-0.01M ammonium acetate (V:V, 10:90), the analysis method is acetonitrile—the mobile phase A=70:30(V:V), performance period is 10 min.

EXAMPLES

Compound (I), i.e. 3-(4-(dihexylamino)-3-fluorophenyl)-2,6-dimethylpyrimidin-4(3H)-one was prepared according to the synthesis method disclosed in example 24 of patent application WO 2014012360.

Example 1: 3-(4-(dihexylamino)-3-fluorophenyl)-2, 6-dimethylpyrimidin-4(3H)-one Hydrochloride Crystal-I 1. Preparation of 3-(4-(dihexylamino)-3-fluorophenyl)-2,6-dimethylpyrimidin-4(3H)-one Hydrochloride Crystal-I Method One:
3-(4-(Dihexylamino)-3-fluorophenyl)-2,6-dimethylpyrimidin-4(3H)-one (5.01 g) was dissolved in methyl tert-butyl ether (200.0 mL), hydrochloride ethyl acetate solution (5.0 mL, 15.55 mmol) prepared by self was added to the solution dropwise. After the addition, the mixture was stirred at r.t. overnight and filtered by suction. The filter cake was dried under vacuum at 50° C. for 6.5 hours and triturated with ethyl acetate (30.0 mL) and ethanol (10.0 mL) for 24 hours. The mixture was filtered, the filter cake was dried under vacuum at 50° C. overnight to give a white solid product (3.75 g, 68.6%).
Method Two:
3-(4-(Dihexylamino)-3-fluorophenyl)-2,6-dimethylpyrimidin-4(3H)-one (0.4 g) was dissolved in ethyl acetate (8.0 mL), hydrochloride ethyl acetate solution (0.4 mL, 1.24 mmol) prepared by self was added to the solution dropwise, and then ethyl acetate (8.0 mL) was added. The mixture was stirred at r.t. for 5 hours and filtered by suction. The filter cake was dried under vacuum at r.t. to give a white solid product (0.372 g, 85.27%).
Method Three:
3-(4-(Dihexylamino)-3-fluorophenyl)-2,6-dimethylpyrimidin-4(3H)-one (5.24 g) was dissolved in isopropanol (40.0 mL), to the solution was added seed crystal of hydrochloride crystal-I (200 mg, synthesis method see method one or method two), and then added hydrochloride isopropanol solution (1.9 g, 15.6 mmol). The mixture was stirred at rt overnight to precipitate crystal, and filtered by suction. The filter cake was washed with isopropanol (5.0 mL×2) and dried under vacuum overnight to give a white solid product (5.29 g, 92.9%).

2. Identification of 3-(4-(dihexylamino)-3-fluorophenyl)-2,6-dimethylpyrimidin-4(3H)-one Hydrochloride Crystal-I (1) The XRPD pattern was analyzed and identified by using Empyrean X-ray powder diffraction (XRPD) with Cu-Kα radiation, having the following characteristic peaks expressed in degrees 2θ at 3.68°, 7.25°, 10.88°, 11.53°, 12.43°, 12.74°, 13.63°, 14.47°, 14.77°, 15.23°, 16.82°, 17.30°, 17.65°, 18.16°, 19.43°, 20.19°, 21.41°, 21.83°, 22.20°, 22.90°, 23.28°, 23.79°, 24.13°, 24.64°, 24.99°, 25.51°, 25.97°, 26.67°, 27.30°, 27.73°, 28.86°, 29.33°, 29.88°, 31.02°, 31.81°, 32.39°, 32.83°, 34.05°, 34.48°, 35.69°, 36.56°, 37.07° and 37.83°. The error margin in 2θ of the characteristic peaks is ±0.2°.

(2) The infrared spectroscopy was analyzed and identified by using TENSOR 27 infrared spectrometer, having the following absorption peaks at 606, 656, 721, 756, 819, 878, 911, 964, 981, 1028, 1078, 1101, 1117, 1153, 1166, 1198, 1215, 1265, 1290, 1343, 1366, 1397, 1435, 1455, 1464, 1512, 1538, 1592, 1616, 1633, 1665, 1694, 1738, 1822, 1957, 2342, 2355, 2555, 2724, 2754, 2857, 2930, 2956, 3024, 3046, 3183, 3256, 3324, 3374, 3419, 3432, 3453, 3459, 3479, 3493 and 3500 cm$^{-1}$. The error margin in 2θ of the characteristic peaks is ±0.2°.

Example 2: 3-(4-(dihexylamino)-3-fluorophenyl)-2, 6-dimethylpyrimidin-4(3H)-one Hydrochloride Crystal-II 1. Preparation of 3-(4-(dihexylamino)-3-fluorophenyl)-2,6-dimethylpyrimidin-4(3H)-one Hydrochloride Crystal-II 3-(4-(Dihexylamino)-3-fluorophenyl)-2,6-dimethylpyrimidin-4(3H)-one hydrochloride crystal-I (10 g) was added to acetic acid (40 mL), the mixture was heated to 80° C. until the solid was dissolved completely. The mixture was kept at 80° C. for 2.0 hours and cooled to r.t. slowly and stirred to precipitate crystal. The mixture was filtered by suction, the filter cake was washed with a little of acetic acid (2.0 mL) and dried under vacuum at rt to give a white solid product (4.2 g, 42%).

2. Identification of 3-(4-(dihexylamino)-3-fluorophenyl)-2,6-dimethylpyrimidin-4(3H)-one Hydrochloride Crystal-II (1) The XRPD pattern was analyzed and identified by using Empyrean X-ray powder diffraction (XRPD) with Cu-Kα radiation, having the following characteristic peaks expressed in degrees 2θ at 6.12°, 8.83°, 12.27°, 13.54°, 13.80°, 13.97°, 15.56°, 16.51°, 17.24°, 18.48°, 19.69°, 21.81°, 22.68°, 23.80°, 24.70°, 25.24°, 25.72°, 26.35°, 26.66°, 27.17°, 27.50°, 28.12°, 29.03°, 30.43°, 31.03°, 31.56° and 37.58°. The error margin in 2θ of the characteristic peaks is ±0.2°.

(2) The infrared spectroscopy was analyzed and identified by using TENSOR 27 infrared spectrometer, having the following absorption peaks at 667, 727, 757, 882, 969, 1026, 1039, 1081, 1109, 1159, 1199, 1291, 1365, 1396, 1439, 1457, 1478, 1509, 1545, 1593, 1611, 1666, 1729, 2524, 2550, 2581, 2684, 2871, 2934, 2955, 3010, 3257 and 3377 cm$^{-1}$. The error margin in 2θ of the characteristic peaks is ±0.2°.

Example 3: 3-(4-(dihexylamino)-3-fluorophenyl)-2,6-dimethylpyrimidin-4(3H)-one Hydrochloride Crystal-III

1. Preparation of 3-(4-(dihexylamino)-3-fluorophenyl)-2,6-dimethylpyrimidin-4(3H)-one Hydrochloride Crystal-III 3-(4-(Dihexylamino)-3-fluorophenyl)-2,6-dimethylpyrimidin-4(3H)-one (5.24 g) was added into the mixed solvent of N-methylpyrrolidone and water (V:V=4:1, 2.0 mL), the solution was cooled to −15° C., and added with hydrochloride isopropanol solution (90 µL, Wt=30%) and the mixed solvent of N-methylpyrrolidone and water (V:V=4:1, 0.5 mL). The mixture was filtered by suction, the filter cake was washed with methyl tert-butyl ether (1.0 mL×3) and dried under vacuum at r.t. to give a white solid product (142 mg, 67.4%).

2. Identification of 3-(4-(dihexylamino)-3-fluorophenyl)-2,6-dimethylpyrimidin-4(3H)-one Hydrochloride Crystal-III The XRPD pattern was analyzed and identified by using Empyrean X-ray powder diffraction (XRPD) with Cu-Kα radiation, having the following characteristic peaks expressed in degrees 2θ at 3.46°, 6.80°, 10.25°, 11.51°, 11.93°, 12.77°, 13.62°, 14.77°, 17.26°, 18.95°, 19.83°, 20.56°, 21.64°, 22.57°, 23.09°, 24.10°, 26.44°, 26.66°, 27.35°, 28.41°, 29.09°, 30.50°, 31.67°, 34.16°, 37.13° and 39.38°. The error margin in 2θ of the characteristic peaks is ±0.2°.

Example 4: 3-(4-(dihexylamino)-3-fluorophenyl)-2,6-dimethylpyrimidin-4(3H)-one Sulfate Crystal-I

1. Preparation of 3-(4-(dihexylamino)-3-fluorophenyl)-2,6-dimethylpyrimidin-4(3H)-one Sulfate Crystal-I 3-(4-(Dihexylamino)-3-fluorophenyl)-2,6-dimethylpyrimidin-4(3H)-one (0.602 g) was dissolved in ethyl acetate (8.0 mL), and to the solution was added concentrated sulfuric acid (0.5 mL). The mixture was stirred at r.t. overnight, and filtered by suction. The filter cake was washed with ethyl acetate to give a white solid product (0.64 g, 85.45%).

2. Identification of 3-(4-(dihexylamino)-3-fluorophenyl)-2,6-dimethylpyrimidin-4(3H)-one Sulfate Crystal-I The XRPD pattern was analyzed and identified by using Empyrean X-ray powder diffraction (XRPD) with Cu-Kα radiation, having the following characteristic peaks expressed in degrees 2θ at 3.35°, 6.61°, 7.89°, 9.90°, 10.45°, 12.74°, 13.20°, 14.86°, 15.22°, 16.50°, 16.87°, 17.30°, 18.40°, 19.03°, 19.43°, 19.65°, 20.56°, 20.87°, 21.43°, 21.74°, 23.19°, 23.45°, 23.80°, 24.60°, 25.29°, 25.90°, 26.07°, 26.40°, 27.26°, 28.22°, 28.47°, 30.82°, 31.75°, 33.80°, 34.55°, 36.77°, 37.30° and 39.02°. The error margin in 2θ of the characteristic peaks is ±0.2°.

Example 5: 3-(4-(dihexylamino)-3-fluorophenyl)-2,6-dimethylpyrimidin-4(3H)-one Sulfate Amorphism

1. Preparation of 3-(4-(dihexylamino)-3-fluorophenyl)-2,6-dimethylpyrimidin-4(3H)-one Sulfate Amorphism 3-(4-(Dihexylamino)-3-fluorophenyl)-2,6-dimethylpyrimidin-4(3H)-one (0.42 g) was dissolved in ethyl acetate (3.0 mL), to the solution was added concentrated sulfuric acid (0.1 mL). The mixture was stirred at r.t. overnight, and filtered by suction. The filter cake was washed with ethyl acetate and dried under vacuum at r.t. to give a white solid product (0.428 g, 81.92%).

Figure 6:
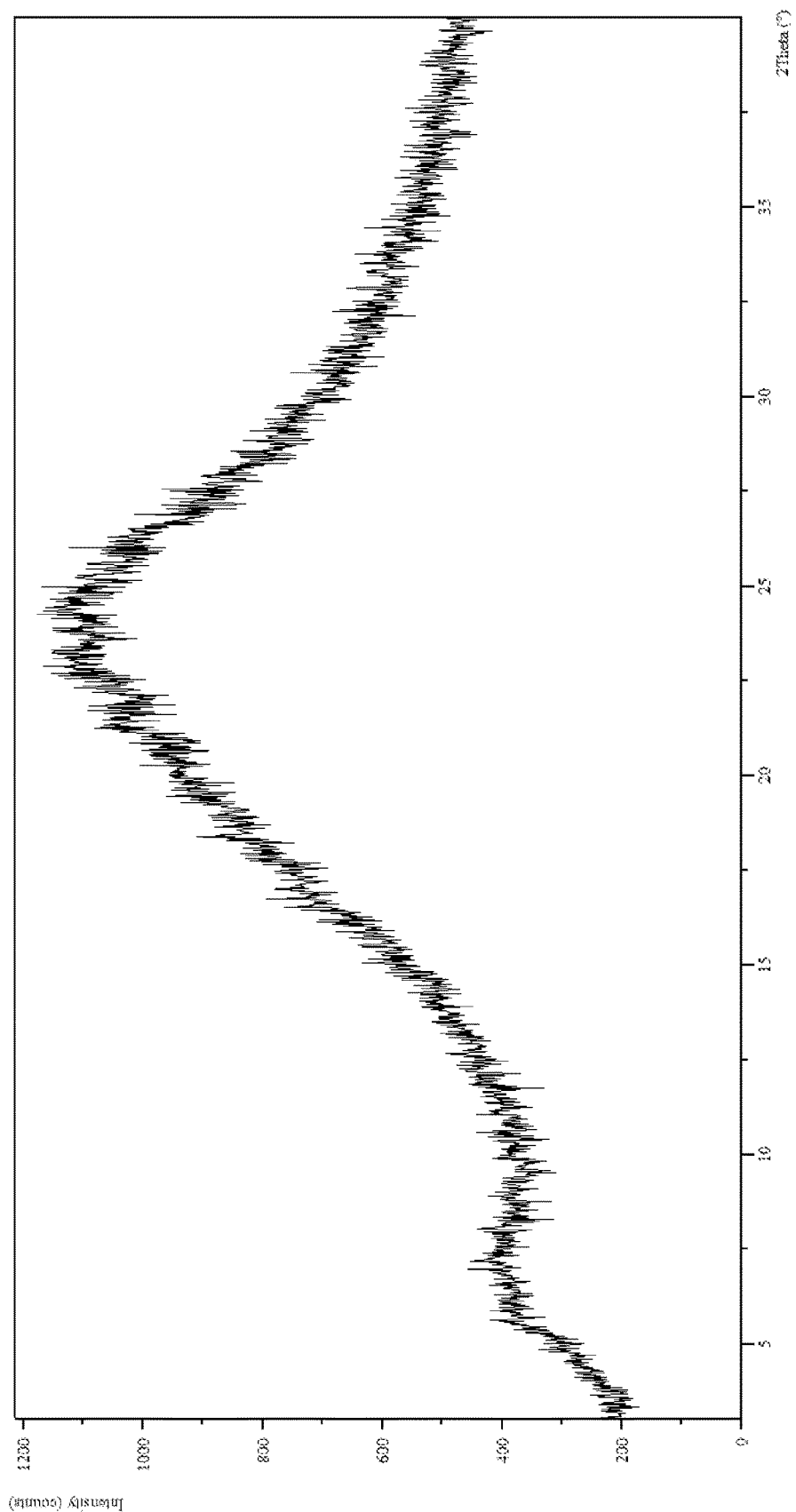
FIG. 6 shows that the X-ray powder diffraction pattern of sulfate amorphism of the compound of formula (I)

2. Identification of 3-(4-(dihexylamino)-3-fluorophenyl)-2,6-dimethylpyrimidin-4(3H)-one Sulfate Amorphism The XRPD pattern was analyzed and identified by using Empyrean X-ray powder diffraction (XRPD) substantially as shown in FIG. 6.

Example 6: 3-(4-(dihexylamino)-3-fluorophenyl)-2,6-dimethylpyrimidin-4(3H)-one Tosilate Crystal-I

1. Preparation of 3-(4-(dihexylamino)-3-fluorophenyl)-2,6-dimethylpyrimidin-4(3H)-one Tosilate Crystal-I 3-(4-(Dihexylamino)-3-fluorophenyl)-2,6-dimethylpyrimidin-4(3H)-one (0.201 g) was dissolved in butanone (5.0 mL), to the solution was added p-toluenesulfonic acid monohydrate (0.238 g). The mixture was stirred at r.t. overnight, and filtered by suction. The filter cake was washed with n-heptane to give a white solid product (0.23 g, 61.6%).

2. Identification of 3-(4-(dihexylamino)-3-fluorophenyl)-2,6-dimethylpyrimidin-4(3H)-one Tosilate Crystal-I (1) The XRPD pattern was analyzed and identified by using Empyrean X-ray powder diffraction (XRPD) with Cu-Kα radiation, having the following characteristic peaks expressed in degrees 2θ at 6.55°, 8.18°, 8.68°, 9.37°, 9.60°, 9.97°, 10.80°, 11.05°, 12.80°, 13.18°, 13.74°, 13.96°, 15.48°, 16.41°, 17.18°, 17.44°, 17.87°, 18.18°, 18.97°, 19.83°, 20.08°, 20.31°, 20.95°, 21.32°, 22.17°, 22.47°, 22.99°, 23.79°, 24.02°, 24.86°, 25.44°, 26.27°, 26.83°, 27.32°, 27.65°, 28.10°, 29.06°, 30.39°, 30.87°, 31.57°, 32.04°, 33.18° and 36.87°. The error margin in 2θ of the characteristic peaks is ±0.2°.

The DSC thermogram was analyzed and identified by using TA Q2000 differential scanning calorimetry (DSC) with a scan rate of 10° C./minute, comprising an endothermic peak at 231.51° C. The error margin of the endothermic peaks is ±3° C.

Example 7: 3-(4-(dihexylamino)-3-fluorophenyl)-2,6-dimethylpyrimidin-4(3H)-one Tosilate Amorphism

1. Preparation of 3-(4-(dihexylamino)-3-fluorophenyl)-2,6-dimethylpyrimidin-4(3H)-one Tosilate Amorphism 3-(4-(Dihexylamino)-3-fluorophenyl)-2,6-dimethylpyrimidin-4(3H)-one tosilate crystal-I (3.0 g) was dissolved in anhydrous methanol (30 mL), the mixture was heated to dissolve. The solution was spayed by a spray dryer to give a white powder product.

Figure 9:
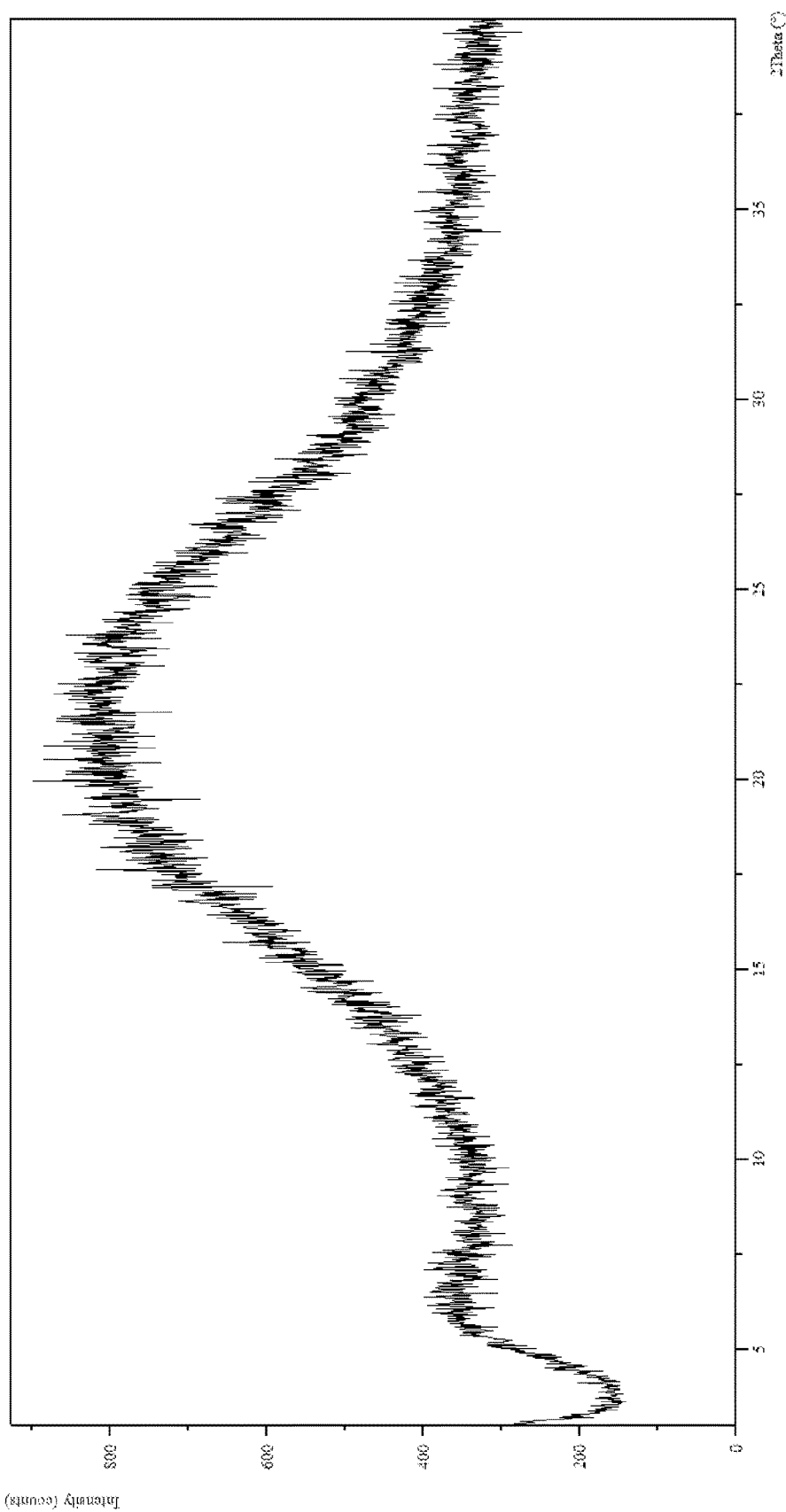
FIG. 9 shows that the X-ray powder diffraction pattern of tosilate amorphism of the compound of formula (I)

2. Identification of 3-(4-(dihexylamino)-3-fluorophenyl)-2,6-dimethylpyrimidin-4(3H)-one Tosilate Amorphism The XRPD pattern was analyzed and identified by using Empyrean X-ray powder diffraction (XRPD) substantially as shown in FIG. 9.

Example 8: 3-(4-(dihexylamino)-3-fluorophenyl)-2,6-dimethylpyrimidin-4(3H)-one Maleate Crystal-I

1. Preparation of 3-(4-(dihexylamino)-3-fluorophenyl)-2,6-dimethylpyrimidin-4(3H)-one Maleate Crystal-I 3-(4-(Dihexylamino)-3-fluorophenyl)-2,6-dimethylpyrimidin-4(3H)-one (407 mg) was dissolved in ethyl acetate (1.5 mL), to the solution was added maleic acid (129 mg). The mixture was stirred at r.t. overnight and concentrated in vacuo. The residue was triturated with n-heptane (6.0 mL) for 2.5 hours and filtered by suction. The filter cake was washed with n-heptane and dried under vacuum at r.t. to give a white solid product (0.45 g, 85.79%).

2. Identification of 3-(4-(dihexylamino)-3-fluorophenyl)-2,6-dimethylpyrimidin-4(3H)-one Maleate Crystal-I (1) The XRPD pattern was analyzed and identified by using Empyrean X-ray powder diffraction (XRPD) with Cu-Kα radiation, having the following characteristic peaks expressed in degrees 2θ at 4.10°, 8.01°, 8.16°, 12.23°, 13.94°, 14.31°, 15.32°, 16.33°, 16.82°, 17.72°, 18.38°, 18.39°, 19.14°, 19.77°, 20.45°, 20.95°, 21.58°, 22.34°, 23.87°, 24.63°, 25.56°, 26.43°, 27.51°, 28.24°, 28.78°, 29.62°, 30.13°, 30.93°, 33.01°, 35.58° and 37.37°. The error margin in 2θ of the characteristic peaks is ±0.2°.

(2) The DSC thermogram was analyzed and identified by using TA Q2000 differential scanning calorimetry (DSC) with a scan rate of 10° C./minute, comprising an endothermic peak at 116.28° C. The error margin of the endothermic peaks is ±3° C.

Example 9: Pharmacokinetics Experiments of the Salts of the Invention

Compound (I) disclosed herein, ie. (3-(4-(dihexylamino)-3-fluorophenyl)-2,6-dimethylpyrimidin-4(3H)-one), crystalline forms of the various salts were filled into capsules, which were administered orally.

Male Beagle dogs (6-10 kg) were grouped randomly, each group had 3 numbers, one group was administered compound (I), others were administered various salts with a dosage of 5 mg/kg. Blood samples were collected at 0.25, 0.5, 1.0, 2.0, 4.0, 6.0, 8.0, 12 and 24 hours after the administration. Standard curve was plotted based on concentrations of the samples in a suitable range, the concentrations of test compounds in plasma samples were determined by using Agilent 6430 LC-MS/MS under MRM mode, and quantitative analysis was performed. Pharmacokinetic parameters were calculated according to drug concentration-time curve using a noncompartmental method by WinNonLin 6.3 software. The results were shown as table 1.

TABLE 1

Pharmacokinetics experiments data of the salts of the invention

| Test sample | $T_{max}$ (h) | $C_{max}$ (ng/ml) | $AUC_{last}$ (h * ng/ml) | $AUC_{INF}$ (h * ng/ml) | $T_{1/2}$ (h) | $MRT_{INF}$ (h) |
|---|---|---|---|---|---|---|
| Compound (I) | 1.17 | 244 | 1730 | 2320 | 13.8 | 23.3 |
| Example 1 | 2.33 | 364 | 4470 | 6310 | 34.5 | 41.9 |
| Example 2 | 8.83 | 485 | 2940 | 2820 | 9.54 | 9.43 |
| Example 6 | 2 | 329 | 2720 | 3010 | 17.5 | 17.5 |
| Example 8 | 2 | 588 | 5859.22 | 38337.53 | 110.28 | 155.21 |

Conclusion:

It can be known from table 1 that the salts of compound (I) have a higher exposure compared to the free 3-(4-(dihexylamino)-3-fluorophenyl)-2,6-dimethylpyrimidin-4(3H)-one (ie. compound (I)), wherein example 1 (hydrochloride crystal-I), example 2 (hydrochloride crystal-II), example 6 (tosilate crystal-I) and example 8 (maleate crystal-I) have a relative higher exposure.

Example 10: Stability Experiments of the Salts of the Invention

High temperature test: an appropriate amount of sample was put in a weighing bottle in the form of a thin layer of ≤5 mm, under a temperature of 60° C. for 10 days. Samples were took at fifth and tenth day, appearance was observed and purity was detected by HPLC. The results were shown as table 2.

TABLE 2

High temperature test of the salts of the invention

| Test sample | | Example 1 | Example 2 | Example 6 | Example 8 |
|---|---|---|---|---|---|
| appearance | 0 d | white powder | white powder | white powder | white solid |
| | 5 d | white powder | white powder | white powder | white to pale yellow solid |
| | 10 d | white powder | white powder | white powder | white to pale yellow solid |
| Purity/% | 0 d | 99.81 | 99.85 | 99.83 | 99.53 |
| | 5 d | 99.80 | 99.86 | 99.81 | 99.49 |
| | 10 d | 99.79 | 99.83 | 99.81 | 99.05 |

High humidity test: an appropriate amount of sample was put in a weighing bottle in the form of a thin layer of ≤5 mm, under a temperature of 25° C. and RH 90%±5% for 10 days. Samples were took at fifth and tenth day, appearance was observed and purity was detected by HPLC. The results were shown as table 3.

TABLE 3

High humidity test of the salts of the invention

| Test sample | | Example 1 | Example 2 | Example 6 | Example 8 |
|---|---|---|---|---|---|
| appearance | 0 d | white powder | white powder | white powder | white solid |
| | 5 d | white powder | white powder | white powder | white solid |
| | 10 d | white powder | white powder | white powder | white solid |
| purity/% | 0 d | 99.81 | 99.85 | 99.83 | 99.53 |
| | 5 d | 99.79 | 99.86 | 99.80 | 99.51 |
| | 10 d | 99.80 | 99.82 | 99.83 | 99.49 |

Conclusion:

It can be known from table 2 and 3 that appearance and purity of the salts of the invention have no significant change at high temperature (60° C.) and high humidity (25° C., RH 90%±5%), and the salts of the invention have a good stability and are suitable for drug formulation.

Example 11: Hygroscopicity Experiments of the Salts of the Invention

Hygroscopicity of an appropriate amount of sample was detected on dynamic moisture absorption instrument. The results showed that the salts provided herein are not easy to be influenced by high humidity to deliquesce.

The above contents are merely basic descriptions under the idea of the present invention, any equivalent modifications based on the technical schemes of the invention are all within the claimed scope of the invention.

Reference throughout this specification to "an embodiment," "some embodiments," "one embodiment", "another example," "an example," "a specific examples," or "some examples," means that a particular feature, structure, material, or characteristic described in connection with the embodiment or example is included in at least one embodiment or example of the present disclosure. Thus, the appearances of the phrases such as "in some embodiments," "in one embodiment", "in an embodiment", "in another example, "in an example," "in a specific examples," or "in some examples," in various places throughout this specification are not necessarily referring to the same embodiment or example of the present disclosure. Furthermore, the particular features, structures, materials, or characteristics may be combined in any suitable manner in one or more embodiments or examples.

Although explanatory embodiments have been shown and described, it would be appreciated by those skilled in the art that the above embodiments cannot be construed to limit the present disclosure, and changes, alternatives, and modifications can be made in the embodiments without departing from spirit, principles and scope of the present disclosure.

What is claimed is:

1. A pharmaceutically acceptable acid addition salt of compound (I),

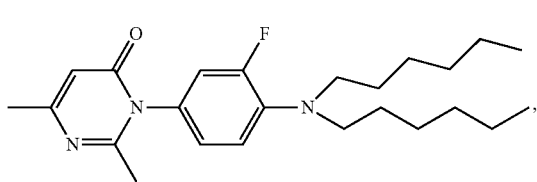

wherein the salt is hydrochloride crystal-I, which is characterized by an X-ray powder diffraction pattern comprising peaks expressed as 2θ at 3.68±0.2°, 10.88±0.2°, 17.30±0.2°, 22.20±0.2°, and 26.67±0.2°; or the salt is hydrochloride crystal-II, which is characterized by an X-ray powder diffraction pattern comprising peaks expressed as 2θ at 6.12±0.2°, 8.83±0.2°, 15.56±0.2°, 19.69±0.2°, 25.24±0.2°, and 26.35±0.2°; or the salt is hydrochloride crystal-III, which is characterized by an X-ray powder diffraction pattern comprising peaks expressed as 2θ at 3.46±0.2°, 10.25±0.2°, 13.62±0.2°, and 17.26±0.2°; or the salt is sulfate crystal-I, which is characterized by an X-ray powder diffraction pattern comprising peaks expressed as 2θ at 3.35±0.2°, 6.61±0.2°, 16.50±0.2°, and 21.43±0.2°; or the salt is tosilate crystal-I, which is characterized by an X-ray powder diffraction pattern comprising peaks expressed as 2θ at 6.55±0.2°, 13.74±0.2°, 20.08±0.2°, 21.32±0.2°, 22.17±0.2°, and 22.99±0.2°; or the salt is maleate crystal-I, which is characterized by an X-ray powder diffraction pattern comprising peaks expressed as 2θ at 4.10±0.2°, 16.33±0.2°, and 20.45±0.2°.

2. The acid addition salt of claim 1, wherein the salt is hydrochloride crystal-I, which is characterized by an X-ray powder diffraction pattern comprising peaks expressed as 2θ at 3.68±0.2°, 10.88±0.2°, 11.53±0.2°, 12.43±0.2°, 17.30±0.2°, 17.65±0.2°, 19.43±0.2°, 21.83±0.2°, 22.20±0.2°, 22.90±0.2°, 25.51±0.2°, and 26.67±0.2°; or the salt is hydrochloride crystal-II, which is characterized by an X-ray powder diffraction pattern comprising peaks expressed as 2θ at 6.12±0.2°, 8.83±0.2°, 12.27±0.2°, 13.97±0.2°, 15.56±0.2°, 16.51±0.2°, 17.24±0.2°, 18.48±0.2°, 19.69±0.2°, 22.68±0.2°, 25.24±0.2°, and 26.35±0.2°; or the salt is hydrochloride crystal-III, which is characterized by an X-ray powder diffraction pattern comprising peaks expressed as 2θ at 3.46±0.2°, 10.25±0.2°, 13.62±0.2°, 17.26±0.2°, 20.56±0.2°, 24.10±0.2°, 26.44±0.2°, 26.66±0.2°, and 27.35±0.2°; or the salt is sulfate crystal-I, which is characterized by an X-ray powder diffraction pattern comprising peaks expressed as 2θ at 3.35±0.2°, 6.61±0.2°, 13.20±0.2°, 16.50±0.2°, 19.03±0.2°, 21.43±0.2°, and 23.19±0.2°; or the salt is tosilate crystal-I, which is characterized by an X-ray powder diffraction pattern comprising peaks expressed as 2θ at 6.55±0.2°, 13.74±0.2°, 13.96±0.2°, 17.18±0.2°, 17.44±0.2°, 19.83±0.2°, 20.08±0.2°, 20.31±0.2°, 21.32±0.2°, 22.17±0.2°, 22.99±0.2°, and 26.83±0.2°; or the salt is maleate crystal-I, which is characterized by an X-ray powder diffraction pattern comprising peaks expressed as 2θ at 4.10±0.2°, 8.16±0.2°, 16.33±0.2°, 17.72±0.2°, 20.45±0.2°, 21.58±0.2°, and 24.63±0.2°.

3. The acid addition salt of claim 1, wherein the salt is hydrochloride crystal-I, which is characterized by an X-ray powder diffraction pattern comprising peaks expressed as 2θ at 3.68±0.2°, 7.25±0.2°, 10.88±0.2°, 11.53±0.2°, 12.43±0.2°, 12.74±0.2°, 13.63±0.2°, 14.47±0.2°, 14.77±0.2°, 15.23±0.2°, 16.82±0.2°, 17.30±0.2°, 17.65±0.2°, 18.16±0.2°, 19.43±0.2°, 20.19±0.2°, 21.41±0.2°, 21.83±0.2°, 22.20±0.2°, 22.90±0.2°, 23.28±0.2°, 23.79±0.2°, 24.13±0.2°, 24.64±0.2°, 24.99±0.2°, 25.51±0.2°, 25.97±0.2°, 26.67±0.2°, 27.30±0.2°, 27.73±0.2°, 28.86±0.2°, 29.33±0.2°, 29.88±0.2°, 31.02±0.2°, 31.81±0.2°, 32.39±0.2°, 32.83±0.2°, 34.05±0.2°, 34.48±0.2°, 35.69±0.2°, 36.56±0.2°, 37.07±0.2°, and 37.83±0.2°; or
the salt is hydrochloride crystal-II, which is characterized by an X-ray powder diffraction pattern comprising peaks expressed as 2θ at 6.12±0.2°, 8.83±0.2°, 12.27±0.2°, 13.54±0.2°, 13.80±0.2°, 13.97±0.2°, 15.56±0.2°, 16.51±0.2°, 17.24±0.2°, 18.48±0.2°, 19.69±0.2°, 21.81±0.2°, 22.68±0.2°, 23.80±0.2°, 24.70±0.2°, 25.24±0.2°, 25.72±0.2°, 26.35±0.2°, 26.66±0.2°, 27.17±0.2°, 27.50±0.2°, 28.12±0.2°, 29.03±0.2°, 30.43±0.2°, 31.03±0.2°, 31.56±0.2°, and 37.58±0.2°; or
the salt is hydrochloride crystal-III, which is characterized by an X-ray powder diffraction pattern comprising peaks expressed as 2θ at 3.46±0.2°, 6.80±0.2°, 10.25±0.2°, 11.51±0.2°, 11.93±0.2°, 12.77±0.2°, 13.62±0.2°, 14.77±0.2°, 17.26±0.2°, 18.95±0.2°, 19.83±0.2°, 20.56±0.2°, 21.64±0.2°, 22.57±0.2°, 23.09±0.2°, 24.10±0.2°, 26.44±0.2°, 26.66±0.2°, 27.35±0.2°, 28.41±0.2°, 29.09±0.2°, 30.50±0.2°, 31.67±0.2°, 34.16±0.2°, 37.13±0.2°, and 39.38±0.2°; or
the salt is sulfate crystal-I, which is characterized by an X-ray powder diffraction pattern comprising peaks expressed as 2θ at 3.35±0.2°, 6.61±0.2°, 7.89±0.2°, 9.90±0.2°, 10.45±0.2°, 12.74±0.2°, 13.20±0.2°, 14.86±0.2°, 15.22±0.2°, 16.50±0.2°, 16.87±0.2°, 17.30±0.2°, 18.40±0.2°, 19.03±0.2°, 19.43±0.2°, 19.65±0.2°, 20.56±0.2°, 20.87±0.2°, 21.43±0.2°, 21.74±0.2°, 23.19±0.2°, 23.45±0.2°, 23.80±0.2°, 24.60±0.2°, 25.29±0.2°, 25.90±0.2°, 26.07±0.2°, 26.40±0.2°, 27.26±0.2°, 28.22±0.2°, 28.47±0.2°, 30.82±0.2°, 31.75±0.2°, 33.80±0.2°, 34.55±0.2°, 36.77±0.2°, 37.30±0.2°, and 39.02±0.2°; or
the salt is tosilate crystal-I, which is characterized by an X-ray powder diffraction pattern comprising peaks expressed as 2θ at 6.55±0.2°, 8.18±0.2°, 8.68±0.2°, 9.37±0.2°, 9.60±0.2°, 9.97±0.2°, 10.80±0.2°, 11.05±0.2°, 12.80±0.2°, 13.18±0.2°, 13.74±0.2°, 13.96±0.2°, 15.48±0.2°, 16.41±0.2°, 17.18±0.2°, 17.44±0.2°, 17.87±0.2°, 18.18±0.2°, 18.97±0.2°, 19.83±0.2°, 20.08±0.2°, 20.31±0.2°, 20.95±0.2°, 21.32±0.2°, 22.17±0.2°, 22.47±0.2°, 22.99±0.2°, 23.79±0.2°, 24.02±0.2°, 24.86±0.2°, 25.44±0.2°, 26.27±0.2°, 26.83±0.2°, 27.32±0.2°, 27.65±0.2°, 28.10±0.2°, 29.06±0.2°, 30.39±0.2°, 30.87±0.2°, 31.57±0.2°, 32.04±0.2°, 33.18±0.2°, and 36.87±0.2°; or
the salt is maleate crystal-I, which is characterized by an X-ray powder diffraction pattern comprising peaks expressed as 2θ at 4.10±0.2°, 8.01±0.2°, 8.16±0.2°, 12.23±0.2°, 13.94±0.2°, 14.31±0.2°, 15.32±0.2°, 16.33±0.2°, 16.82±0.2°, 17.72±0.2°, 18.38±0.2°, 18.39±0.2°, 19.14±0.2°, 19.77±0.2°, 20.45±0.2°, 20.95±0.2°, 21.58±0.2°, 22.34±0.2°, 23.87±0.2°, 24.63±0.2°, 25.56±0.2°, 26.43±0.2°, 27.51±0.2°, 28.24±0.2°, 28.78±0.2°, 29.62±0.2°, 30.13±0.2°, 30.93±0.2°, 33.01±0.2°, 35.58±0.2°, and 37.37±0.2°.

Figure 3:
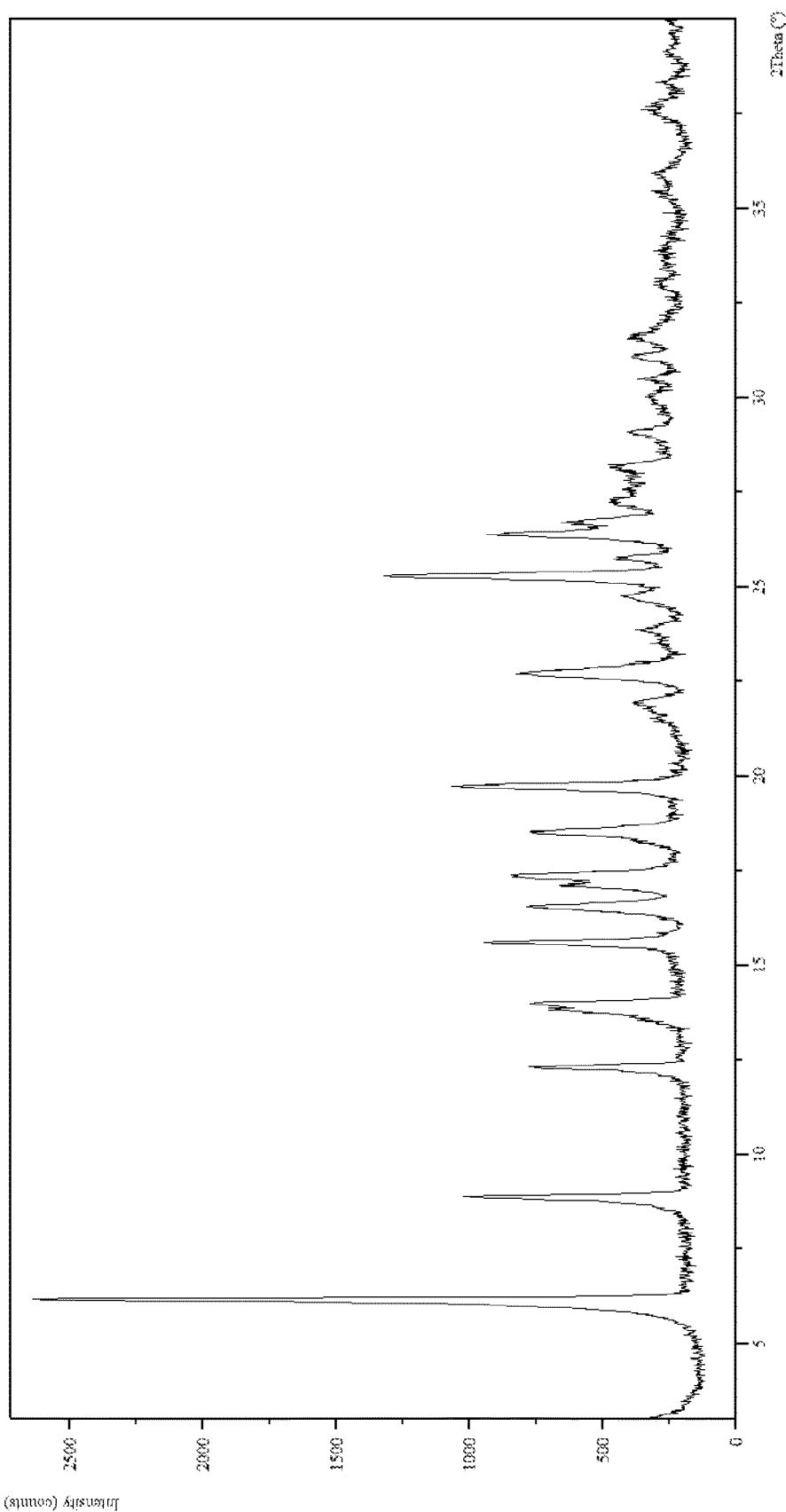
FIG. 3 shows that the X-ray powder diffraction pattern of hydrochloride crystal-II of the compound of formula (I)
Figure 5:
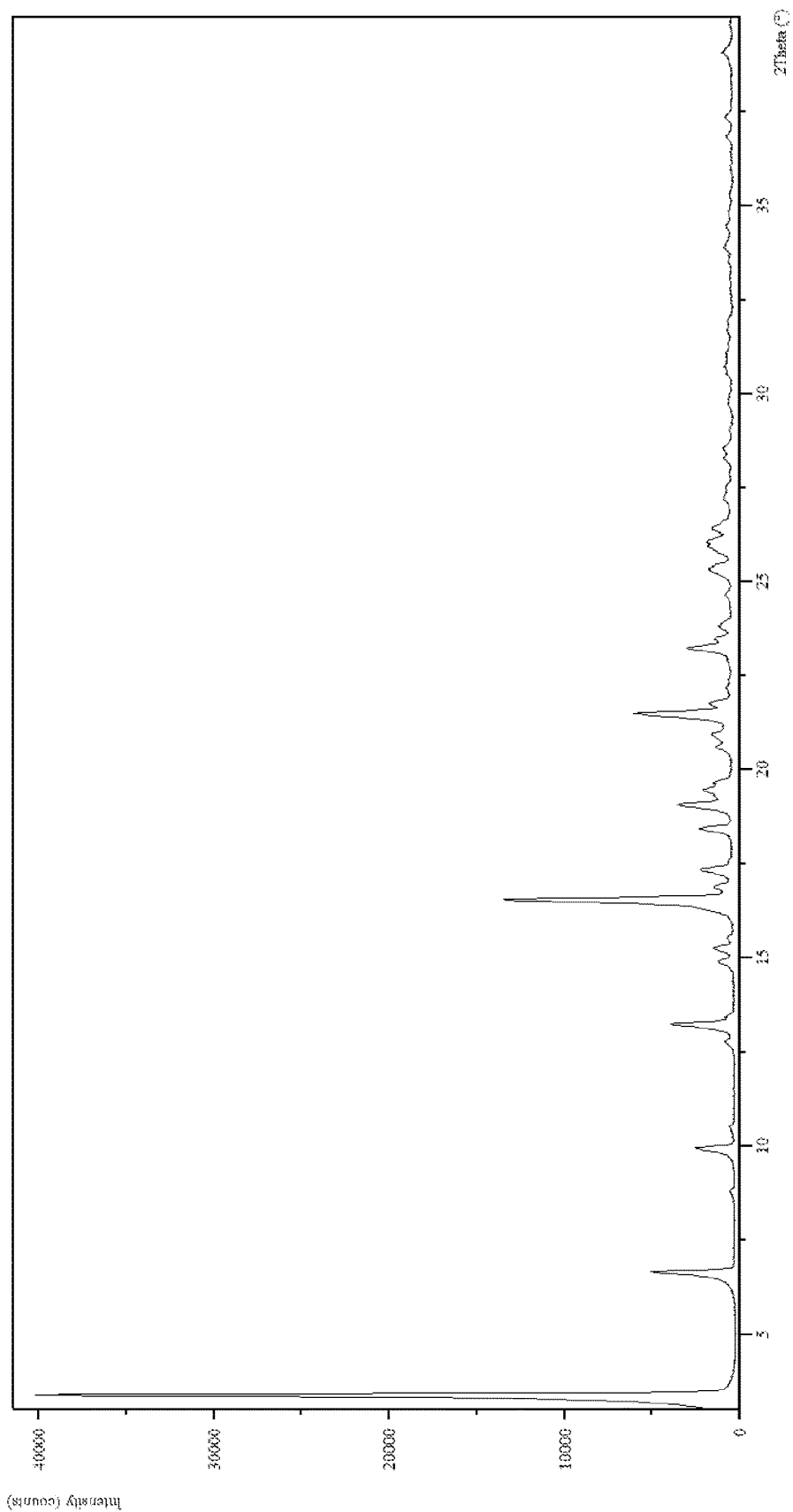
FIG. 5 shows that the X-ray powder diffraction pattern of sulfate crystal-I of the compound of formula (I)
Figure 7:
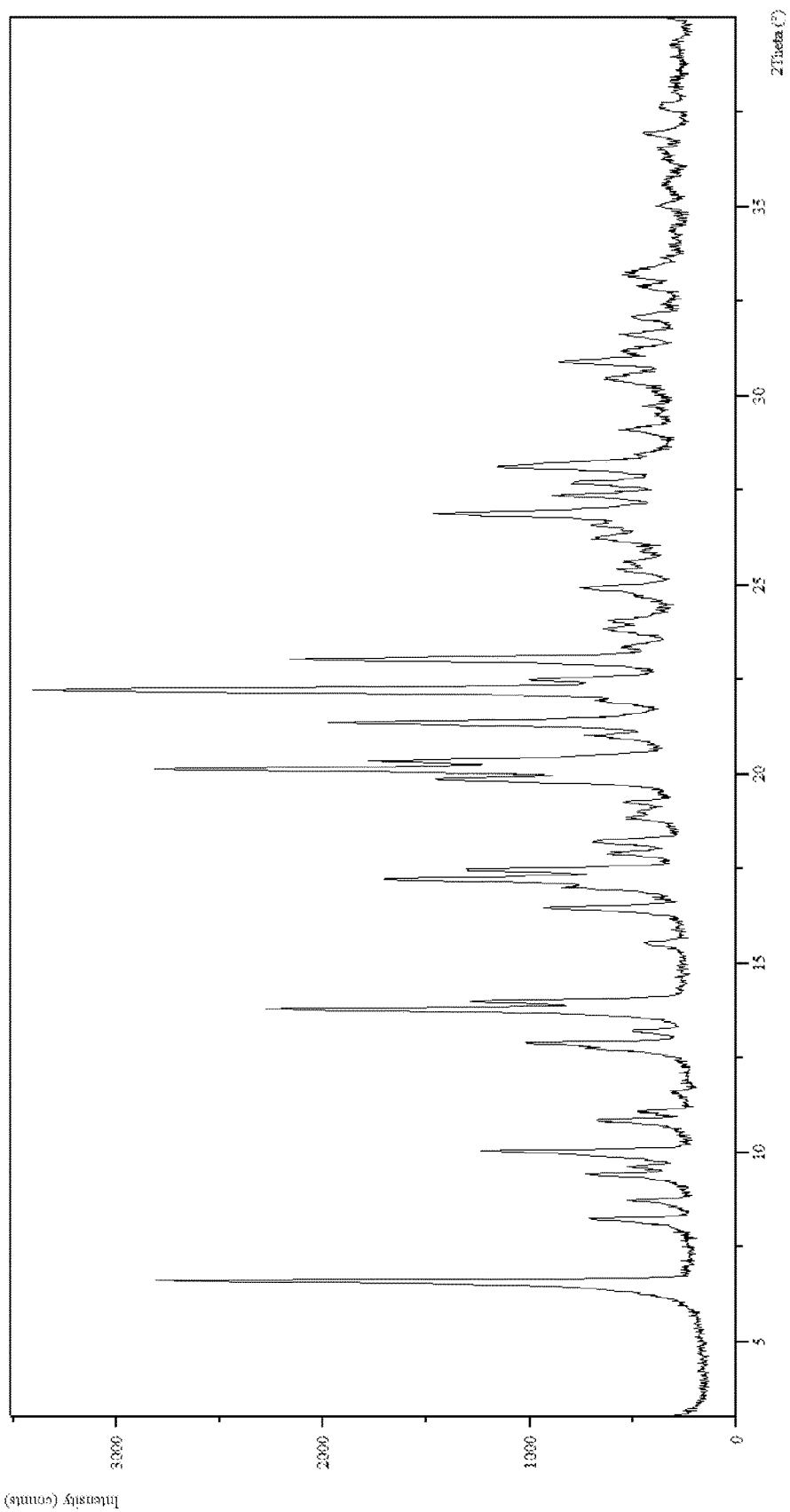
FIG. 7 shows that the X-ray powder diffraction pattern of tosilate crystal-I of the compound of formula (I)
Figure 10:
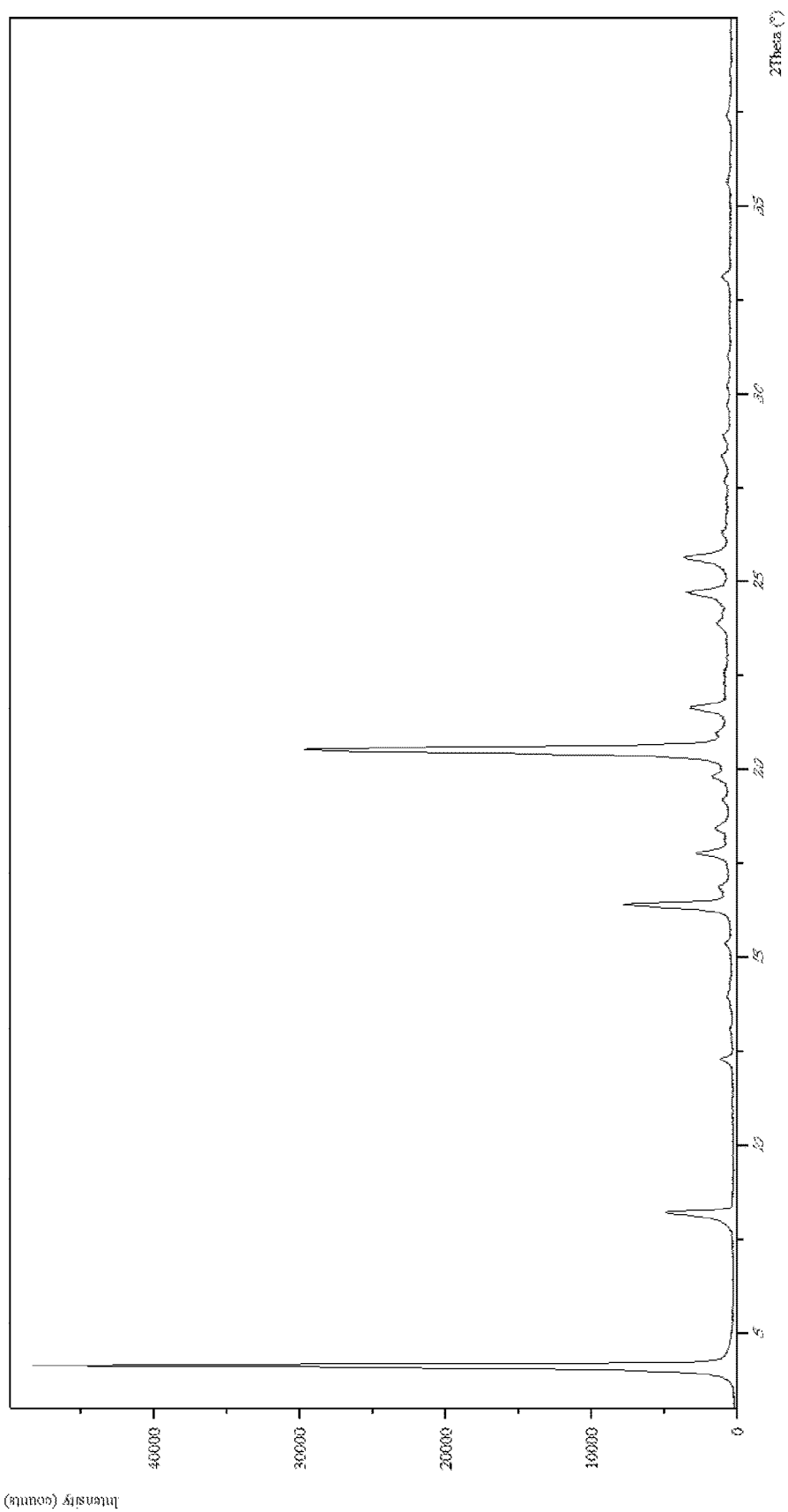
FIG. 10 shows that the X-ray powder diffraction pattern of maleate crystal-I of the compound of formula (I)
Figure 12:
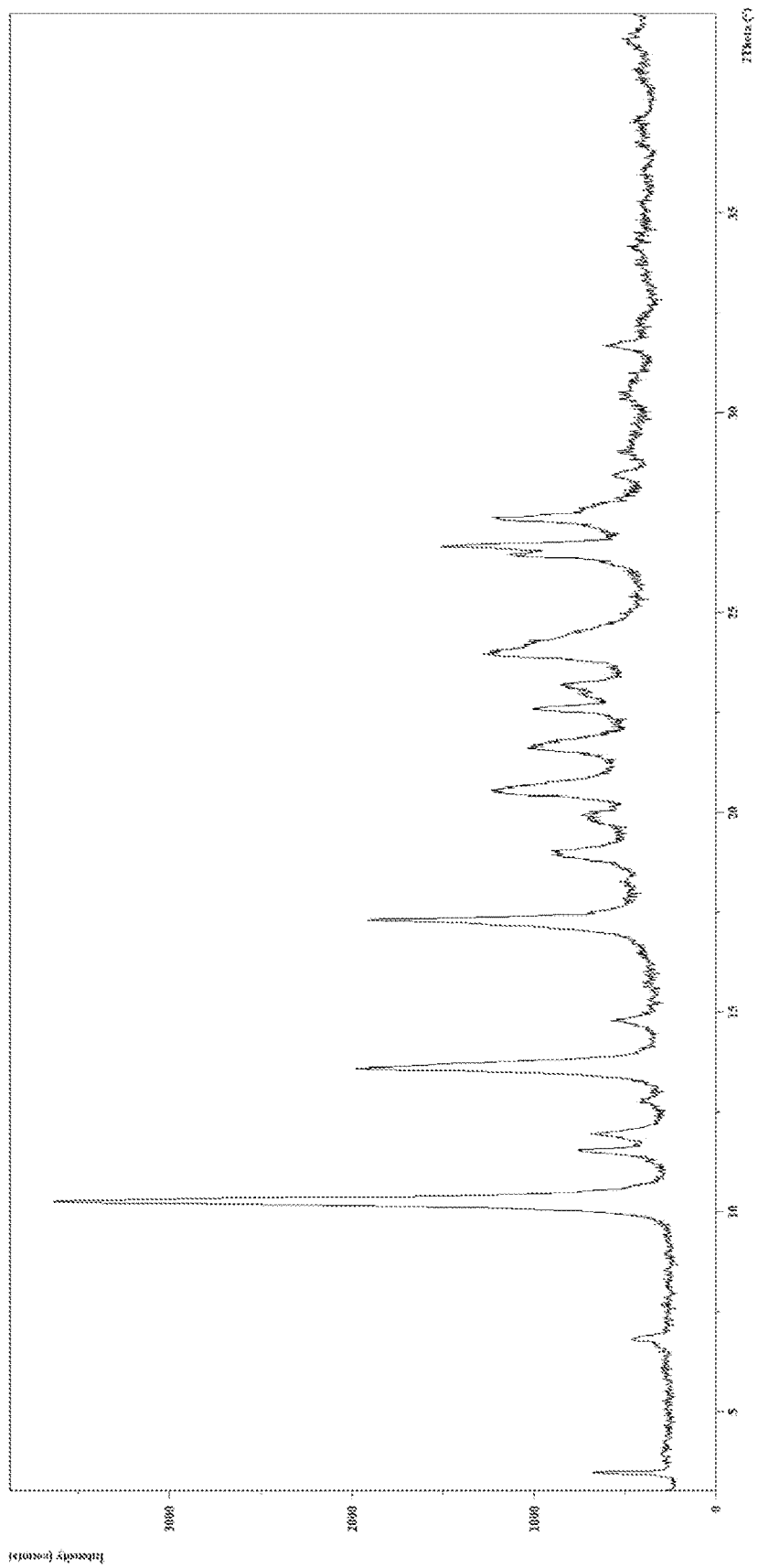
FIG. 12 shows that the X-ray powder diffraction pattern of hydrochloride crystal-III of the compound of formula (I).

4. The acid addition salt of claim 1, wherein the salt is hydrochloride crystal-I, which is characterized by an X-ray powder diffraction pattern as shown in FIG. 1, wherein the error margin in 2θ of the characteristic peaks is ±0.2°; or
the salt is hydrochloride crystal-II, which is characterized by an X-ray powder diffraction pattern as shown in FIG. 3, wherein the error margin in 2θ of the characteristic peaks is ±0.2°; or
the salt is hydrochloride crystal-III, which is characterized by an X-ray powder diffraction pattern as shown in FIG. 12, wherein the error margin in 2θ of the characteristic peaks is ±0.2°; or
the salt is sulfate crystal-I, which is characterized by an X-ray powder diffraction pattern as shown in FIG. 5, wherein the error margin in 2θ of the characteristic peaks is ±0.2°; or
the salt is tosilate crystal-I, which is characterized by an X-ray powder diffraction pattern as shown in FIG. 7, wherein the error margin in 2θ of the characteristic peaks is ±0.2°; or
the salt is maleate crystal-I, which is characterized by an X-ray powder diffraction pattern as shown in FIG. 10, wherein the error margin in 2θ of the characteristic peaks is ±0.2°.

5. The acid addition salt of claim 1, wherein the salt is hydrochloride crystal-I, which is characterized by a Fourier transform infrared spectrogram comprising absorption peaks at 606, 656, 721, 756, 819, 878, 911, 964, 981, 1028, 1078, 1101, 1117, 1153, 1166, 1198, 1215, 1265, 1290, 1343, 1366, 1397, 1435, 1455, 1464, 1512, 1538, 1592, 1616, 1633, 1665, 1694, 1738, 1822, 1957, 2342, 2355, 2555, 2724, 2754, 2857, 2930, 2956, 3024, 3046, 3183, 3256, 3324, 3374, 3419, 3432, 3453, 3459, 3479, 3493 and 3500 cm$^{-1}$; or
the salt is hydrochloride crystal-II, which is characterized by a Fourier transform infrared spectrogram comprising absorption peaks at 667, 727, 757, 882, 969, 1026, 1039, 1081, 1109, 1159, 1199, 1291, 1365, 1396, 1439, 1457, 1478, 1509, 1545, 1593, 1611, 1666, 1729, 2524, 2550, 2581, 2684, 2871, 2934, 2955, 3010, 3257 and 3377 cm$^{-1}$.

Figure 2:
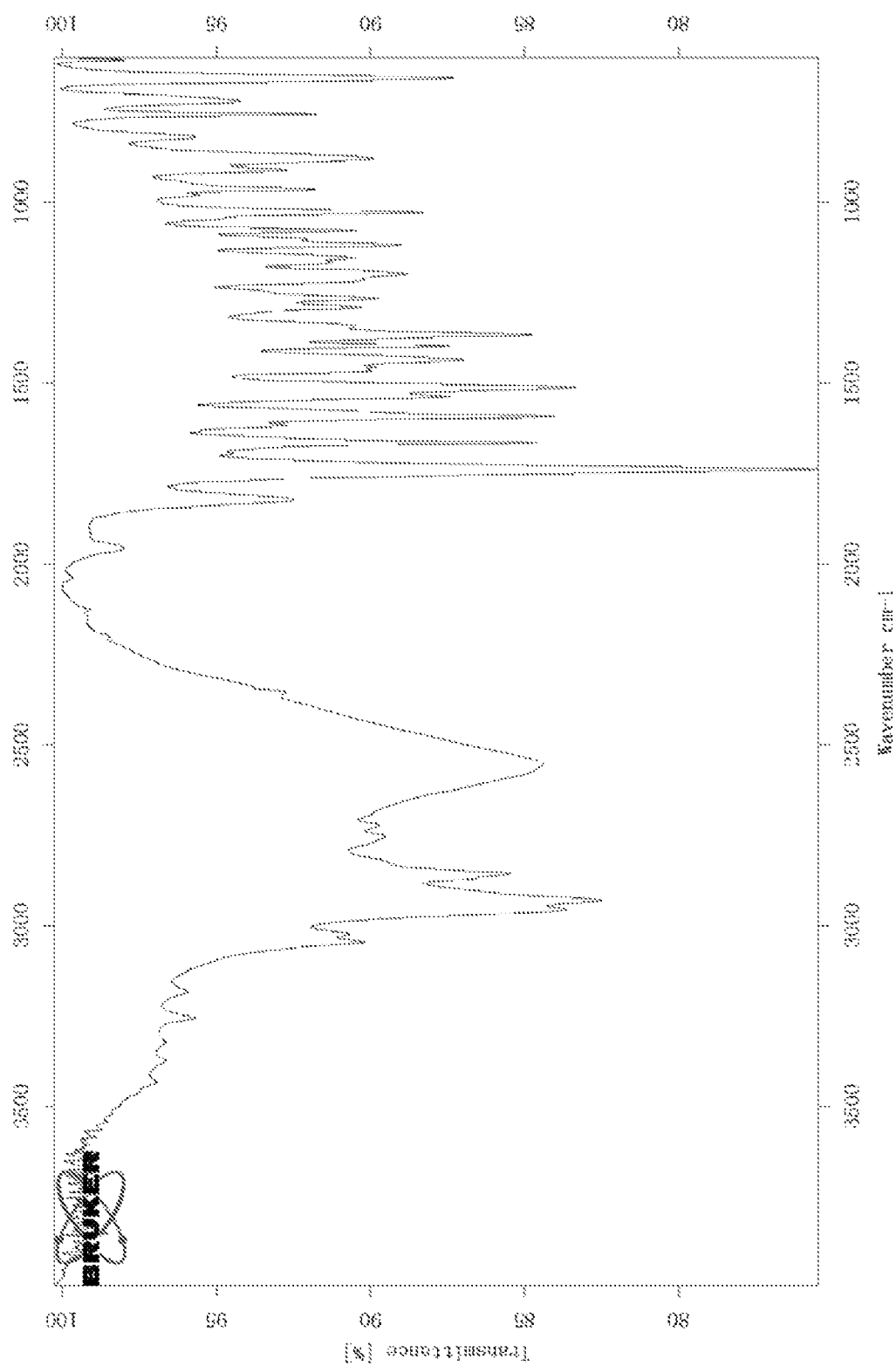
FIG. 2 shows that the Fourier transform infrared spectrogram of hydrochloride crystal-I of the compound of formula (I)
Figure 4:
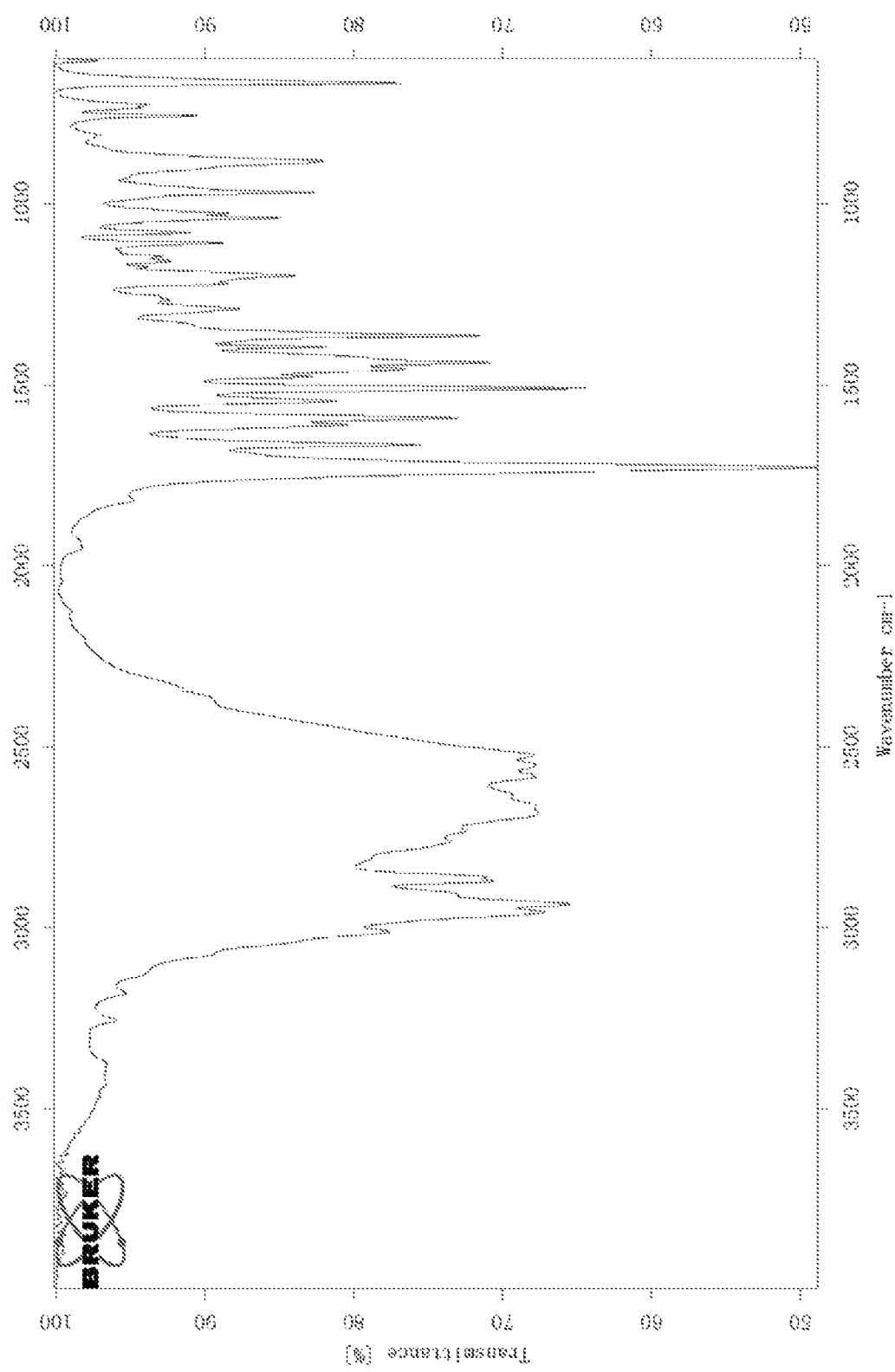
FIG. 4 shows that the Fourier transform infrared spectrogram of hydrochloride crystal-II of the compound of formula (I)

6. The acid addition salt of claim 1, wherein the salt is hydrochloride crystal-I, which is characterized by a Fourier transform infrared spectrogram as shown in FIG. 2, wherein the error margin of the absorption peaks is ±2 cm$^{-1}$; or
the salt is hydrochloride crystal-II, which is characterized by a Fourier transform infrared spectrogram as shown in FIG. 4, wherein the error margin of the absorption peaks is ±2 cm$^{-1}$.

7. The acid addition salt of claim 1, wherein the salt is sulfate amorphism, which is characterized by an X-ray powder diffraction pattern comprising as shown in FIG. 6, wherein the error margin in 2θ of the characteristic peaks is ±0.2°; or
the salt is tosilate amorphism, which is characterized by an X-ray powder diffraction pattern as shown in FIG. 9, wherein the error margin in 2θ of the characteristic peaks is ±0.2°.

8. The acid addition salt of claim 1, wherein the salt is tosilate crystal-I, which is characterized by a differential scanning calorimetry thermogram comprising an endothermic peak at 231.51° C.±3° C.; or the salt is maleate crystal-I, which is characterized by a differential scanning calorimetry thermogram comprising an endothermic peak at 116.28° C.±3° C.

Figure 8:
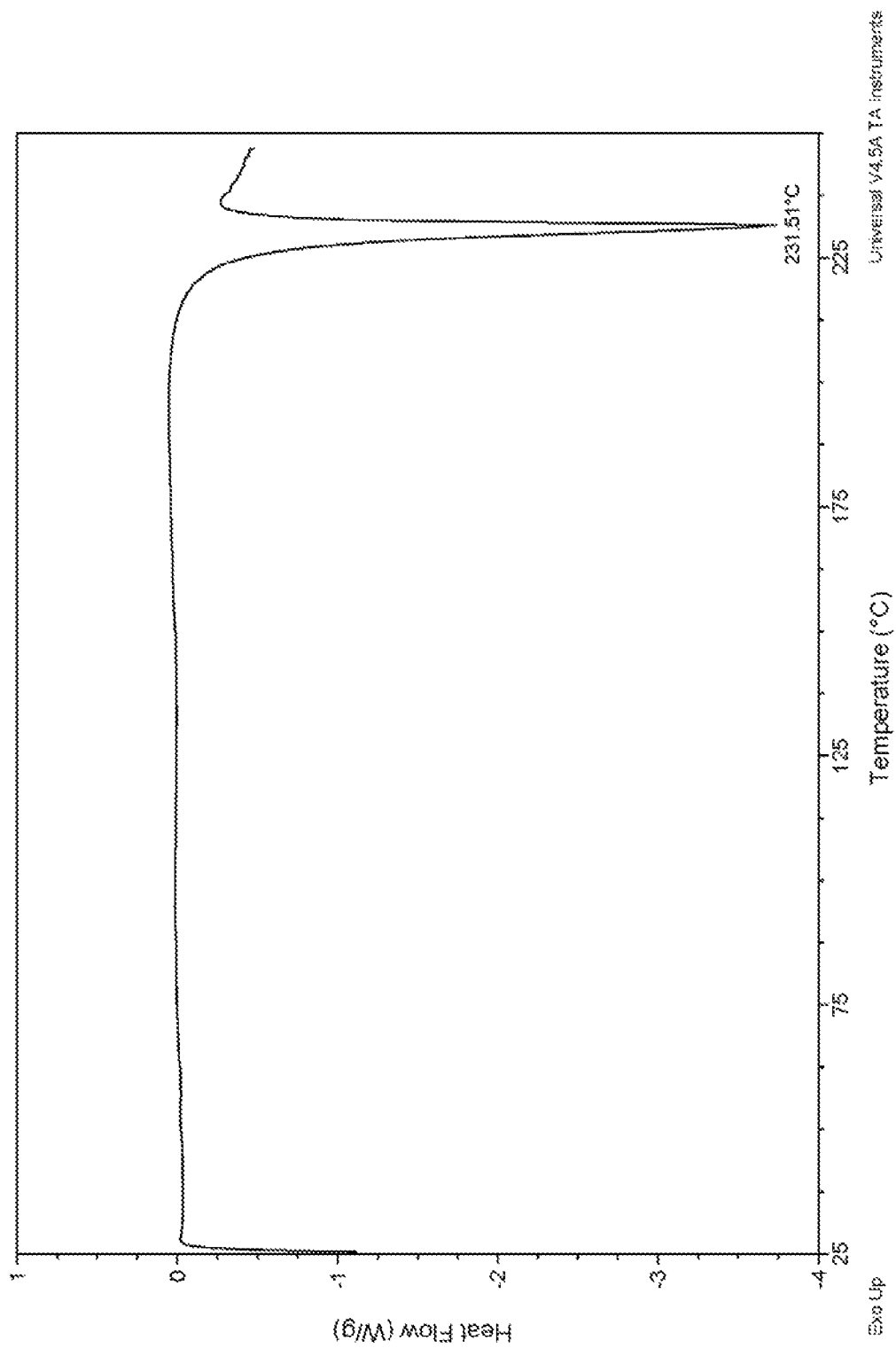
FIG. 8 shows that the differential scanning calorimetry thermogram of tosilate crystal-I of the compound of formula (I)
Figure 11:
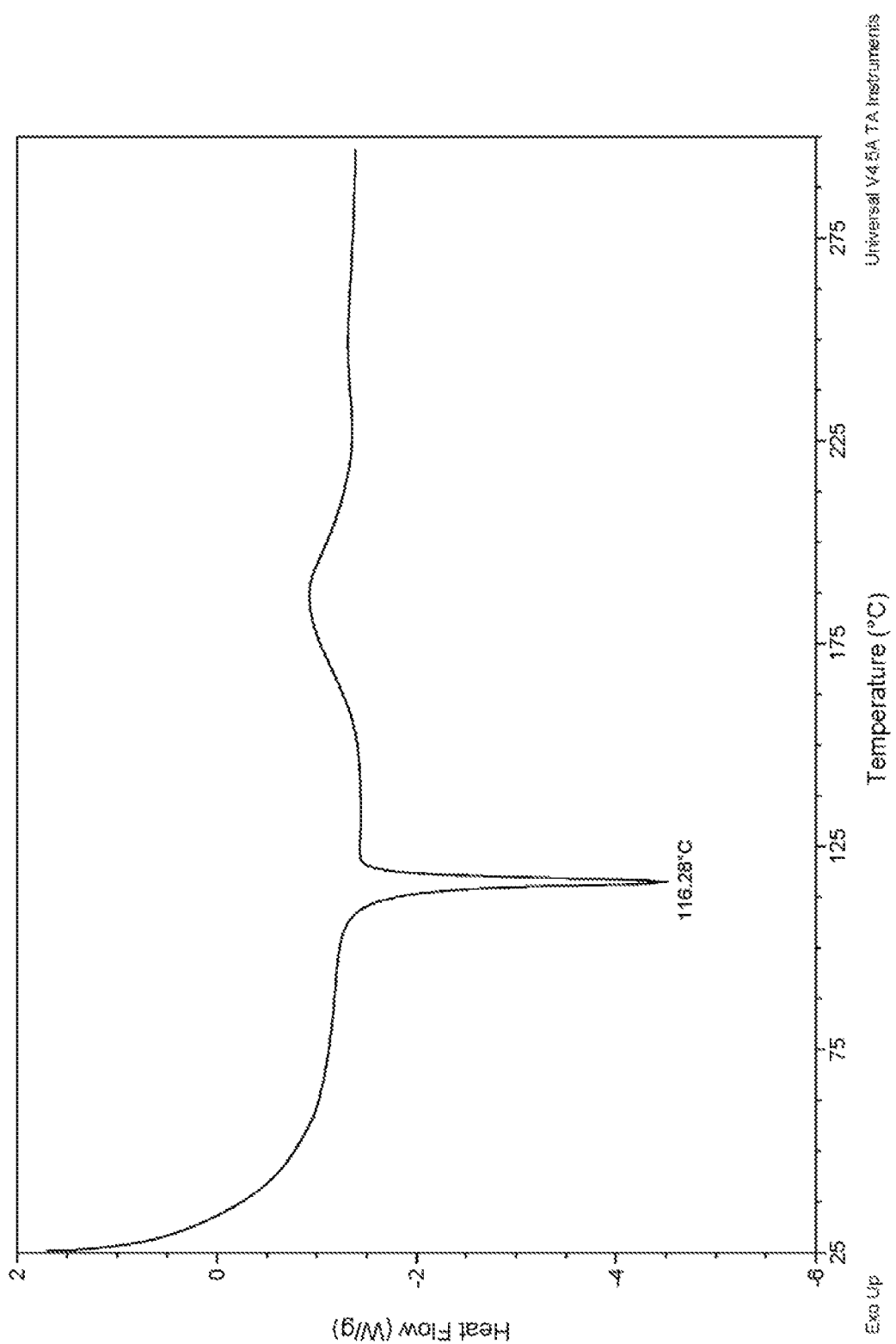
FIG. 11 shows that the differential scanning calorimetry thermogram of maleate crystal-I of the compound of formula (I)

9. The acid addition salt of claim 1, wherein the salt is tosilate crystal-I, which is characterized by a differential scanning calorimetry thermogram as shown in FIG. 8, wherein the error margin in the endothermic peaks is ±3° C.; or the salt is maleate crystal-I, which is characterized by a differential scanning calorimetry thermogram as shown in FIG. 11, wherein the error margin in the endothermic peaks is ±3° C.

10. A pharmaceutical composition comprising the acid addition salt of claim 1, wherein, optionally, the pharmaceutical composition further comprises a pharmaceutically acceptable carrier, excipient, diluent, adjuvant or a combination thereof.

11. A method of treating or lessening a tissue or organ fibrosis disorder comprising administering to a patient with the acid addition salt of claim 1.

12. The method of claim 11, wherein the tissue or organ fibrosis disorder is renal interstitial fibrosis, glomerulosclerosis, liver fibrosis, pulmonary fibrosis, idiopathic pulmonary fibrosis, peritoneal fibrosis, myocardial fibrosis, dermatofibrosis, post-surgery adhesions, benign prostatic hypertrophy, skeletal muscle fibrosis, dermatosclerosis, multiple sclerosis, pancreatic fibrosis, liver cirrhosis, myosarcoma, neurofibroma, pulmonary interstitial fibrosis, diabetic nephropathy, alzheimer disease or vascular fibrosis.

13. A method of treating or lessening a tissue or organ fibrosis disorder comprising administering to a patient with the pharmaceutical composition of claim 10.

14. The method of claim 13, wherein the tissue or organ fibrosis disorder is renal interstitial fibrosis, glomerulosclerosis, liver fibrosis, pulmonary fibrosis, idiopathic pulmonary fibrosis, peritoneal fibrosis, myocardial fibrosis, dermatofibrosis, post-surgery adhesions, benign prostatic hypertrophy, skeletal muscle fibrosis, dermatosclerosis, multiple sclerosis, pancreatic fibrosis, liver cirrhosis, myosarcoma, neurofibroma, pulmonary interstitial fibrosis, diabetic nephropathy, alzheimer disease or vascular fibrosis.

* * * * *